United States Patent
Dolan et al.

(10) Patent No.: US 11,660,104 B2
(45) Date of Patent: May 30, 2023

(54) ENDOVASCULAR APPARATUS

(71) Applicant: Versono Medical Limited, Galway (IE)

(72) Inventors: Finbar Dolan, Galway (IE); Hugh O'Donoghue, Galway (IE); Ivan Mooney, Galway (IE); Pat Connolly, Galway (IE); Jim Smedley, Galway (IE); Brian Tarpey, Galway (IE)

(73) Assignee: Versono Medical Limited, Galway (IE)

( * ) Notice: Subject to any disclaimer, the term of this patent is extended or adjusted under 35 U.S.C. 154(b) by 0 days.

(21) Appl. No.: 17/775,022

(22) PCT Filed: Nov. 6, 2020

(86) PCT No.: PCT/EP2020/081386
§ 371 (c)(1),
(2) Date: May 6, 2022

(87) PCT Pub. No.: WO2021/089847
PCT Pub. Date: May 14, 2021

(65) Prior Publication Data
US 2022/0395285 A1 Dec. 15, 2022

(30) Foreign Application Priority Data

Nov. 6, 2019 (WO) .................. PCT/EP2019/080449
May 5, 2020 (GB) ..................................... 2006665

(51) Int. Cl.
*A61B 17/22* (2006.01)
*A61B 90/00* (2016.01)
*A61B 17/00* (2006.01)

(52) U.S. Cl.
CPC .... *A61B 17/22012* (2013.01); *A61B 17/2202* (2013.01); *A61B 90/39* (2016.02);
(Continued)

(58) Field of Classification Search
CPC .............. A61B 17/221; A61B 17/2204; A61B 17/22012; A61B 2017/22027; A61B 2017/22049; A61B 2017/22094
See application file for complete search history.

(56) References Cited

U.S. PATENT DOCUMENTS

| 3,433,226 A | 3/1969 | Boyd |
| 4,979,939 A | 12/1990 | Shiber |

(Continued)

FOREIGN PATENT DOCUMENTS

| WO | 2019094028 A1 | 5/2019 |
| WO | 2020094747 A2 | 5/2020 |

OTHER PUBLICATIONS

International Search Report and Written Opinion in International Application No. PCT/EP2020/081386, dated Feb. 26, 2021 (10 pages).

*Primary Examiner* — Tuan V Nguyen
(74) *Attorney, Agent, or Firm* — Bookoff McAndrews, PLLC

(57) ABSTRACT

An endovascular apparatus for crossing through an obstruction in a blood vessel comprises: an elongate endovascular element such as a wire; an ultrasonic transducer, mechanically coupled to the endovascular element for ultrasonically exciting a distal tip portion thereof to facilitate the crossing through the obstruction, and one or more damping features, mechanically coupled to the endovascular element to attenuate lateral displacement of the endovascular element at positions away from the distal tip portion.

36 Claims, 28 Drawing Sheets

(52) U.S. Cl.
CPC ............... *A61B 2017/00477* (2013.01); *A61B 2017/22015* (2013.01); *A61B 2017/22027* (2013.01); *A61B 2017/22049* (2013.01); *A61B 2017/22094* (2013.01); *A61B 2090/0808* (2016.02)

(56) References Cited

U.S. PATENT DOCUMENTS

| | | |
|---|---|---|
| 5,248,296 A | 9/1993 | Alliger |
| 5,382,228 A | 1/1995 | Nita et al. |
| 5,427,118 A | 6/1995 | Nita et al. |
| 5,507,738 A * | 4/1996 | Ciervo ............. A61B 17/22012 606/1 |
| 5,542,917 A | 8/1996 | Nita et al. |
| 5,971,949 A | 10/1999 | Levin et al. |
| 6,450,975 B1 | 9/2002 | Brennan et al. |
| 6,855,123 B2 | 2/2005 | Nita |
| 7,831,297 B2 * | 11/2010 | Opie ................. A61B 17/00008 600/585 |
| 9,282,984 B2 | 3/2016 | Nita |
| 9,339,284 B2 * | 5/2016 | Du ................... A61B 17/22012 |
| 9,629,643 B2 | 4/2017 | Nita |
| 9,763,684 B2 * | 9/2017 | Du ................... A61B 17/22012 |
| 2004/0024402 A1 | 2/2004 | Nita |
| 2008/0228111 A1 | 9/2008 | Nita |
| 2016/0331645 A1 * | 11/2016 | Bagwell ............. A61M 3/0279 |

\* cited by examiner

ENDOVASCULAR APPARATUS

TECHNICAL FIELD

The present invention relates to treatment of ischaemia by using an ultrasonically activated wire or other elongate element to cross through a blockage in a blood vessel and to facilitate the introduction of follow-on therapeutic devices.

PRIOR PATENT APPLICATIONS

The invention develops concepts expressed in our International Patent Application published as WO 2020/094747, and the yet unpublished GB patent application no. 2006665.0 whose contents are incorporated herein by reference.

BACKGROUND

In endovascular procedures, an artery is selected and recruited for use in obtaining access to the vasculature. The selection is based on the artery's ability to accommodate the passage of the intended diagnostic or therapeutic device to the target site and the extent to which it may minimise tissue and patient trauma.

In revascularising procedures, for example in peripheral arteries or veins, access is often made by surgical cutdown and puncture to the femoral, popliteal, tibial and/or pedal arteries, commonly known in medical terms as the Seldinger technique. Once the access is made, an introducer wire and an introducer sheath are inserted into the vessel and secured at the site. This sheath acts as a port for the introduction, withdrawal and exchange of devices and serves to minimise abrasion of the arterial tissue. Then guide catheters and guidewires are introduced into the artery, to provide further protection and to assist device navigation and provision of therapy to the target site.

Guidewires are pushed along the lumen of the vessel, carefully to avoid causing any trauma to the vessel wall, and are navigated to the site of the obstruction. In successful procedures, the guidewires are then pushed across, or through, the obstruction and are kept in situ to act as a guide over which the diagnostic or therapeutic devices, such as balloon catheters and stents, are tracked to the site of the occlusion. Guidewires are used in other minimally-invasive procedures to introduce other devices and instruments into vessels or other cavities of the body to enable inspection, diagnosis and different types of treatment.

Guidewires are, for example, used for balloon angioplasty, gastrointestinal, urological, and gynaecological procedures. All such procedures require a passageway to be formed through a blockage to facilitate the passage of larger and often more cumbersome devices to the site of lesions or other tissues targeted distal to the lesions in the body.

Guidewires are key to therapeutic intervention and are manufactured from different materials, most typically stainless steels and various alloys, including NiTi (nitinol), with many different designs. Their manufacture often involves the modification of the chemical composition and microstructural morphology of the material, for example by cold working the material while forming it into a wire and then machining the wire to different dimensional designs and applying different thermal treatments to effect a desirable performance. As an example, specific tapers may be machined over the length of a wire to produce differential degrees of flexibility along the length of the wire. So, at its distal end, the wire will have sufficient flexibility to conform to the shape of the vessel, and strength to transmit force to the tip ('tip stiffness') or force to cross through the lesion.

In conventional guidewires, the tapered segments are encased in coils or jacketing materials that allow for flexibility through the tapers while enabling transmission of force to the distal tip of the wire through the coils. As will be explained, in wires of the invention, such coils or jacketing materials are not essential as force is transmitted by ultrasonic energy to excavate a lumen even if the wire is uncoated or unjacketed.

The length of wires used in endovascular procedures varies depending on the distance over which they are considered likely to operate. As an example, wires typically of 750 mm up to 900 mm in length are used in many peripheral applications where they may be introduced in femoral or popliteal anatomies, or need to track to and through blockages in ipsilateral iliac femoral popliteal and infra popliteal arteries. Wires that are used in ipsilateral and coronary applications tend to be of the order of 1200 mm, 1500 mm or 1700 mm in length. Indeed, wires that may be tracked contra laterally may be longer, perhaps of the order of 2000 mm to 2250 mm or 2500 mm or 3000 mm in length. The most common wire lengths on the market are 1750 mm, 1950 mm and 3000 mm.

In many instances extension wires may be used to facilitate the deployment of certain therapeutic devices. In this instance the proximal end of the wire may require certain features.

Many conventional endovascular wires are passive mechanical devices with no active components. Passive wires do not transmit any energy other than that applied by the clinician. They are operated by their proximal end being pushed, pulled, and torqued to navigate to the blockage site and are then pushed through or around the blockage. They are of varied constructions and designs to facilitate access and crossing of lesions in different anatomies and for different devices. However, in very many instances the occlusions are too challenging for conventional wires to cross through. These passive wires then do not work as guidewires are intended to, or they are limited when trying to cross nearly- or totally-occluded blockages that may also be significantly calcified. In situations where they are tracked around occlusions, e.g. in a sub-intimal situation, such wires are often unsuccessful at re-entering the true lumen.

The present invention relates to the use of ultrasonic vibrations transmitted along wires to cross blockages. Transmission of ultrasonic vibrations along small-diameter catheters and assemblies is disclosed in U.S. Pat. No. 3,433,226. U.S. Pat. No. 5,971,949 describes the transmission of ultrasonic energy via waveguides of different configurations and tip geometries. U.S. Pat. No. 5,427,118 describes an ultrasonic guidewire system but does not discuss in detail proximal geometries of the wire or how it facilitates follow-on devices via over-the-wire methods.

Many current single-transducer systems are not ultrasonically activated guidewires but are instead, ultrasonically activated catheters that contain wire members to agitate and ablate material. U.S. Pat. Nos. 6,855,123 and 4,979,939 describe such systems. These catheters themselves require a separate passive guidewire to help them navigate and, as such, are tools to facilitate a separate guidewire crossing a blockage. U.S. Pat. No. 9,629,643 shows a system with a range of distal tip configurations but all requiring a separate guidewire for access.

These devices are directed towards delivering an alternative method of revascularisation and are often described as atherectomy devices, crossing devices or vessel preparation devices. With limited exceptions, they do not identify with crossing through lesions with the purpose of acting as a device delivery system. In the art, these ultrasonic devices and recanalisation wire devices enhance revascularisation and provide for, or effect, an atherectomy by de-bulking the lesion by removing the plaque that forms the lesion.

In the early, later and current designs, ultrasonic generator systems are large because of the acoustics used and they have become large units, scaled to generate multiple frequencies and to control the pulsed wave. Also, practical utility considerations mean that known systems commonly comprise separate elements. For example, many systems are designed with the signal generator housed in a separate unit from a transducer, some being mounted on large trolley units, consoles or stands that take up significant space in the clinical environment. U.S. Pat. No. 6,450,975, US 2008/0228111 and U.S. Pat. No. 9,282,984 all describe such systems.

Ultrasonically-activated catheter and wire systems have been considered in the past as a method of atherectomy and to prepare vessels for angioplasty treatment. Some products have been made available commercially in the past, some remain available on the market and some new systems have come to market recently. Such catheter and wire systems often include an ultrasonic generator and an ultrasonic transducer. The ultrasonic generator converts mains electricity into an ultrasonic waveform, defined by its voltage amplitude, current and frequency. The ultrasonic transducer, and often an amplifying horn, convert the electrical energy into high-frequency mechanical vibrations, defined by frequency and amplitude of vibration.

A small-diameter wire waveguide is coupled at its proximal end directly to the transducer, or via any horn, and transmits the mechanical vibrations to the distal tip of the wire. This results in the distal tip of the wire waveguide vibrating at a desired amplitude and frequency with the goal of excavating material and ultimately facilitating the revascularisation or recanalisation of vessels and anatomical structures throughout the body. Tissue and material in the vicinity of the distal tip are affected by a combination of the ultrasonic movement of the tip and its direct mechanical abrasion, ablation and cavitation from the pressure wave components and acoustic streaming that removes ablated material from the zone around the tip.

In known ultrasonically activated endovascular wire systems, the proximal end of the guide wire is connected to the transducer. In our patent application published as WO 2020/094747, the wire runs through the transducer and not only extends distally therefrom, but also proximally. This allows the user to couple the transducer to the wire at any desired position and to adjust the total length of the distal portion of the wire, without having to cut it. An adjustable total length of the distal portion of the wire can be very useful for practical purposes, for example to adapt to the expected length of the trajectory the wire tip needs to travel within the patient's body. Also, control of the wire is enhanced in keeping its placement in situ in the vascular lumen whilst adjusting or reconnecting activation source. Additionally, an adjustable-length distal portion of the wire helps for achieving and optimising resonance at the distal tip at any desired frequency.

When using ultrasonic energy to excite the wire, it is desirable to maximise displacement amplitude at the distal tip of the wire to excavate a lesion. Conversely, in the event of a guidewire that extends proximally from the transducer, it is desirable to minimise displacement or movement of that proximal portion of the wire, which is outside the patient's body and indeed may hang freely from the proximal side of the activation unit.

It is an aim of the present invention to address one or more disadvantages associated with the prior art.

SUMMARY OF THE INVENTION

To achieve this aim, an endovascular apparatus for crossing through an obstruction in a blood vessel is provided. The endovascular apparatus comprises an elongate endovascular wire, an ultrasonic transducer and one or more damping features. The ultrasonic transducer is mechanically coupled to or in contact with the elongate endovascular wire for ultrasonically exciting a distal tip thereof to facilitate crossing through the obstruction. The one or more damping features are mechanically coupled to the elongate endovascular wire to attenuate a lateral displacement of the elongate endovascular wire at certain positions away from the distal tip. For example, damping may be applied or effected proximal to the coupling to the transducer to attenuate proximal wave transmission and distal to that coupling to dampen lateral displacement of the wire portion that remains outside the vasculature.

With the endovascular apparatus according to the invention, it is possible to maximise the displacement amplitude at the distal tip of the wire in an energy-efficient way. For optimal efficiency, it is important that a large portion of the power provided by the transducer is passed on to the distal tip by longitudinal waves through the wire. Any loss of energy by lateral oscillations of the wire is therefore to be minimised. With the damping features according to the invention, such lateral displacement is reduced and the energy efficiency of the endovascular apparatus is improved. Resistance to breakage of the wire is also improved.

In an embodiment of the endovascular apparatus according to the invention, the one or more damping features are mechanically coupled to the elongate endovascular wire to attenuate lateral displacement of the elongate endovascular wire at one or more positions between the ultrasonic transducer and the distal tip. When trying to improve coupling to longitudinal displacement, limit lateral displacement and improve wire life, damping the lateral motion of the distal portion of the endovascular wire—that is, extending distally from where the wire is coupled to the transducer—is found to provide the best results. A complicating factor in this is that a large part of the distal portion is to be inserted into the patient's body. However, as will be described below, the inventors have found various ways of achieving the desired damping of the wire near the transducer coupling point where the distal section of the wire emerges without compromising, and indeed enhancing, the functionality of the apparatus.

In preferred embodiments, the ultrasonic transducer is comprised in a transducer housing. At least some of the damping features may be provided in or at the transducer housing. Other damping features may be mechanically coupled to the elongate endovascular wire outside the transducer housing. There may be selective damping at discrete damping locations along the wire length.

In preferred embodiments, the ultrasonic transducer is coupled to the elongate endovascular wire in such a way that the elongate endovascular wire extends proximally as well as distally from the ultrasonic transducer. In such embodiments, the one or more damping features may be mechanically coupled to the elongate endovascular wire to attenuate lateral and/or longitudinal displacement of the elongate endovascular wire at one or more positions proximally of the ultrasonic transducer.

By damping longitudinal and lateral motion of the proximal portion of the endovascular wire, such damping features minimise displacement or movement of the end of the wire that is outside the patient's body and that indeed may hang freely from the proximal side of the activation unit. Reducing or even avoiding such unwanted lateral motion of the proximal wire portion is important for ensuring the safety of the user and to avoid damaging expensive and sensitive equipment, including the wire itself.

More generally, the invention provides apparatus that enables selective or preferential control of the activation of the wire in any direction. The wire is an example of an elongate endovascular element that may be used as a waveguide or wave delivery system. For example, the element could be a hybrid of a wire and a catheter. In particular, a proximal portion of the element, for example about the first metre of the element from the proximal end, could have a wire encapsulated in a manner akin to a catheter or a coating, whereas a distal portion of the element extending to the distal end could be an unencapsulated wire. A wire or other element of the invention could be the inner component of an overall wave delivery system.

Many specific embodiments of both the distal and proximal damping features discussed above—in particular, damping both proximal to the transducer and distal to the transducer near the coupling location—are described below with reference to the figures. Some types of damping features are provided inside the transducer housing, others along the wire portion(s) outside the housing. Some damping features are mainly suitable for damping lateral motion of the distal or the proximal wire portions, while others can be used at both ends or sides of the coupling between the wire and transducer. There may be continuous damping along the wire, or selective, stepped or intermittent damping. Damping may also be achieved by adding weight to the wire at one or more discrete locations.

BRIEF DESCRIPTION OF THE DRAWINGS

Embodiments of the invention will now be described by way of example with reference to the accompanying drawings, in which:

FIG. 16b is a cross sectional view of the hand-held ultrasonic activation unit of FIG. 16a.

DETAILED DESCRIPTION

Figure 1:
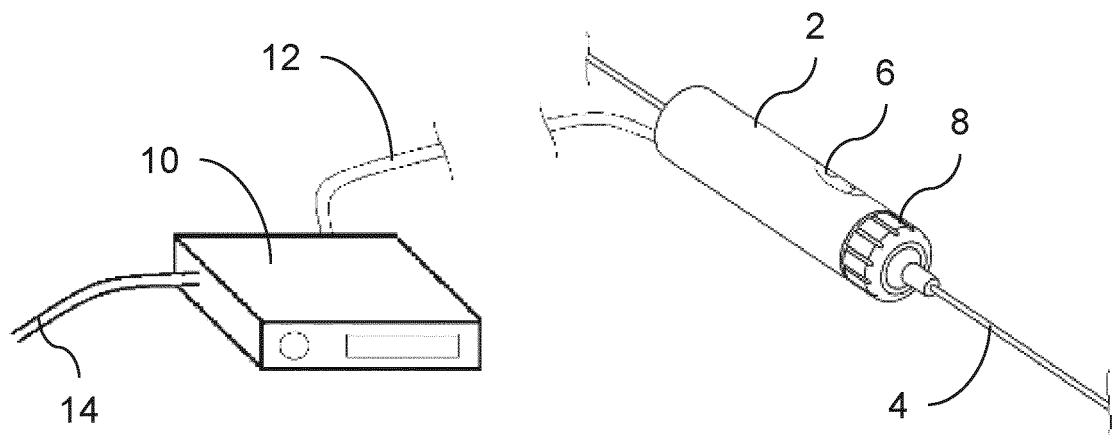
FIG. 1 is a schematic perspective view of an ultrasonic wire system according to the invention.

FIG. 1 of the drawings shows the overall configuration of a system according to the invention and illustrates some major components of such a system. This example features a handheld ultrasonic activation unit 2 through which a flexible transmission member in the form of an endovascular wire 4 extends, in central alignment.

The wire 4 can be inserted into a patient's vasculature and traversed to bring its distal end to the location of a lesion. Once a complex lesion is encountered that resists the wire 4 crossing it, the activation unit 2 can be coupled to the wire 4 at a suitable longitudinal location. When activated, the activation unit 2 transmits ultrasonic vibrations to and along the wire 4, enhancing the ability of the wire 4 to cross the lesion through ablation and other mechanisms. The wire 4 thereby serves as a crossing wire for crossing through an occlusion in a blood vessel and can then remain in situ to serve as a guide wire for delivering subsequent therapeutic devices to treat the lesion.

Typically, the wire 4 may, for example, be more than 2 m and up to 3 m in length. For example, access to a lesion in or through the foot may involve the wire travelling a distance of typically 1200 mm to 2000 mm within the vasculature depending on whether an ipsilateral, contralateral or radial approach is chosen. In this respect, a wire 4 tapering distally to a fine wire at its tip can navigate to the pedal arteries and around the pedal arch between the dorsal and plantar arteries. However, the invention is not limited to pedal or other peripheral applications and could, for example, be used in coronary applications, where the ability of the wire 4 to navigate to and to excavate within tortuous small-diameter arteries is also beneficial.

The diameter of the distal section of the wire 4 will determine the flexibility of the wire 4 and its ability easily to conform to the shape of the anatomy through which it is intended to pass. Thus, for example, in a tortuous (pedal or coronary) anatomy, a distal section of an appropriate length, of a diameter of, for example, 0.005" to 0.007" combines appropriate flexibility with the ability to excavate occlusive material for certain Nitinols.

The activation unit 2 includes user controls 6 and optionally also a display. The activation unit 2 further comprises a distal hand toggle 8 that a user can turn about the central longitudinal axis of the unit 2 and of the wire 4. In particular, the activation unit 2 can slide over the wire 4 and can be coupled to the wire 4 at a plurality of longitudinally-spaced locations by applying torque to turn the toggle 8. To effect coupling, as will be shown in later drawings, the toggle 8 acts on a coupling such as a collet within the activation unit 2 that surrounds and is coaxial with the wire 4. When the toggle 8 is tightened, the collet grips the wire 4 to transmit ultrasonic energy from an integrated ultrasonic transducer within the activation unit 2, optionally via an amplifier horn that is coupled to or integral with the transducer. The wire 4 could be coupled directly to the transducer in some embodiments, in which case the horn may be omitted.

The toggle 8 is reversible to release the activation unit 2 from the wire 4. Provision is thereby made to interchange wires 4 of different dimensions, configurations, or materials for different purposes. There is also the possibility of interchanging the transducer or the horn within the activation unit 2.

FIG. 1 shows a disaggregated arrangement in which an ultrasonic signal generator 10 is separate from the activation unit 2. In this example, the ultrasonic signal generator 10 is connected to the activation unit 2 by a connector cable 12. In alternative arrangements, the ultrasonic signal generator 10 may be incorporated into the housing of the activation unit 2. The example shown in FIG. 1 has an externally-powered ultrasonic signal generator 10 and therefore comprises a power cable 14 that connects to an external source of electrical power. Alternative embodiments may be powered by internal batteries, which can, for example, be incorporated into the ultrasonic signal generator unit 10 or into the activation unit 2.

In general, the components of the system are preferably portable and are more preferably hand-held. The components may be wireless, rechargeable, reusable, and recyclable. Any external cable 12, 14 for conveying power or signals may be coupled through a slip ring to allow free rotation of the cable 12, 14 and to avoid entanglement with the wire 4.

Moving on now to FIGS. 2 to 5, these drawings show various arrangements of the activation unit in longitudinal section. Like numerals are used for like features. In each of these examples, the activation unit 2 is powered externally and is optionally supplied with an ultrasonic signal through a cable 12, although a self-contained battery-powered variant is possible as noted above.

Figure 2:
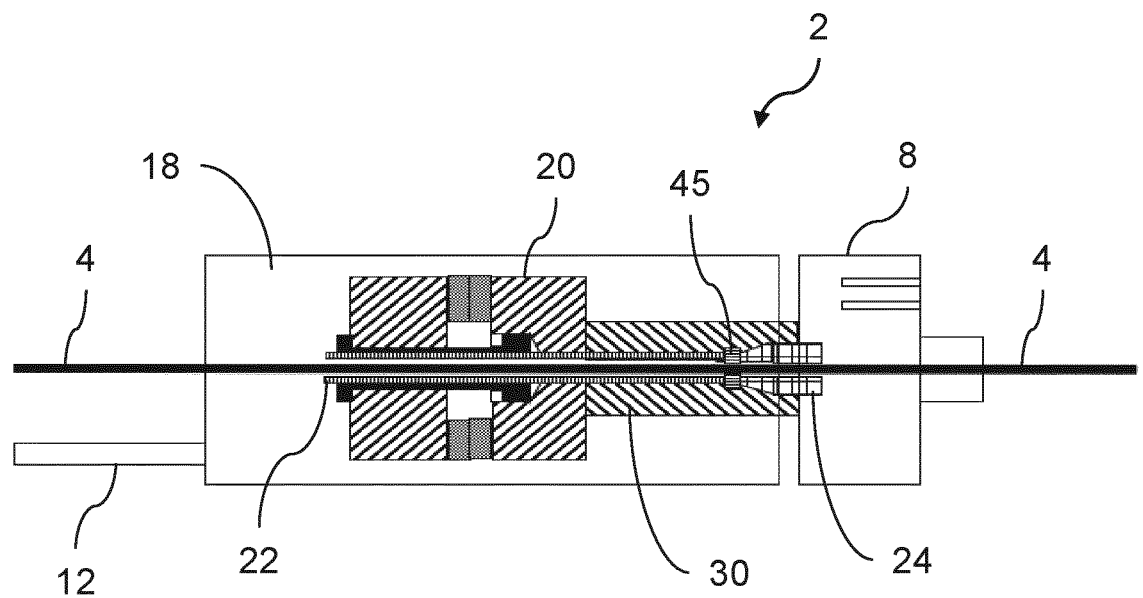
FIG. 2 is a schematic view in longitudinal section of the ultrasonic activation unit shown in FIG. 1.

FIG. 2 shows that the housing 18 of the unit 2 contains an ultrasonic transducer 20 that is penetrated by a central port or lumen 22 to allow for the through-passage of the wire 4. A distal portion of the transducer 20 has a threaded section to allow for the engagement of a collet 24. Various collet concepts will be described later. The wire 4 extends though the full length of the transducer 20 and emerges proximally from the housing 18 in this example. A compressible dampening ring 45 is provided proximally of the collet 24 to help minimize movement of the proximal portion of the wire 4. This dampening ring 45 may be made of an elastic material (i.e. compressible and resilient) such as a polymer or polymer blend.

Figure 3:
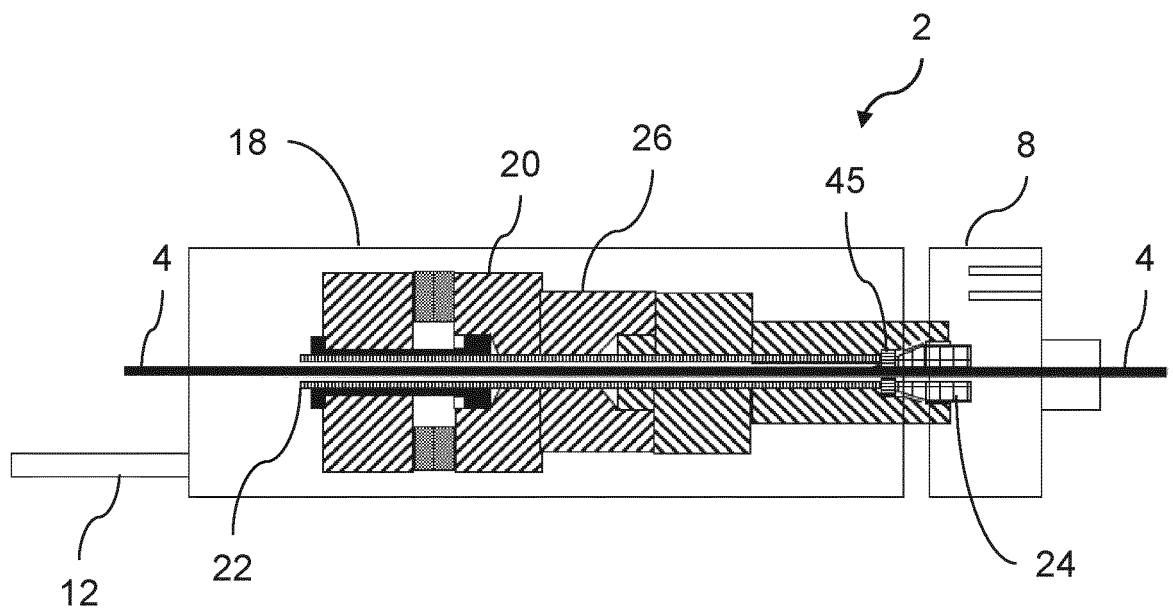
FIG. 3 corresponds to FIG. 2 but shows an acoustic horn coupled to a transducer within a housing of the unit.

FIG. 3 shows another embodiment of the invention in which an acoustic horn 26 is attached to the distal face of the transducer 20. Acoustic horns such as these can be used to amplify the displacement from the distal face of the transducer 20. For this purpose, the horn 26 may taper distally in a continuously-tapered configuration or in a stepped configuration as shown.

In the example shown in FIG. 3, the wire 4 is coupled, via a collet 24, to the distal end or face of the horn 26. The horn 26 has a central lumen 22 or channel that aligns with and communicates with the lumen 22 in the ultrasonic transducer 20. This allows the wire 4 to travel centrally through the horn 26 and transducer 20 along their common longitudinal axis.

Figure 4:
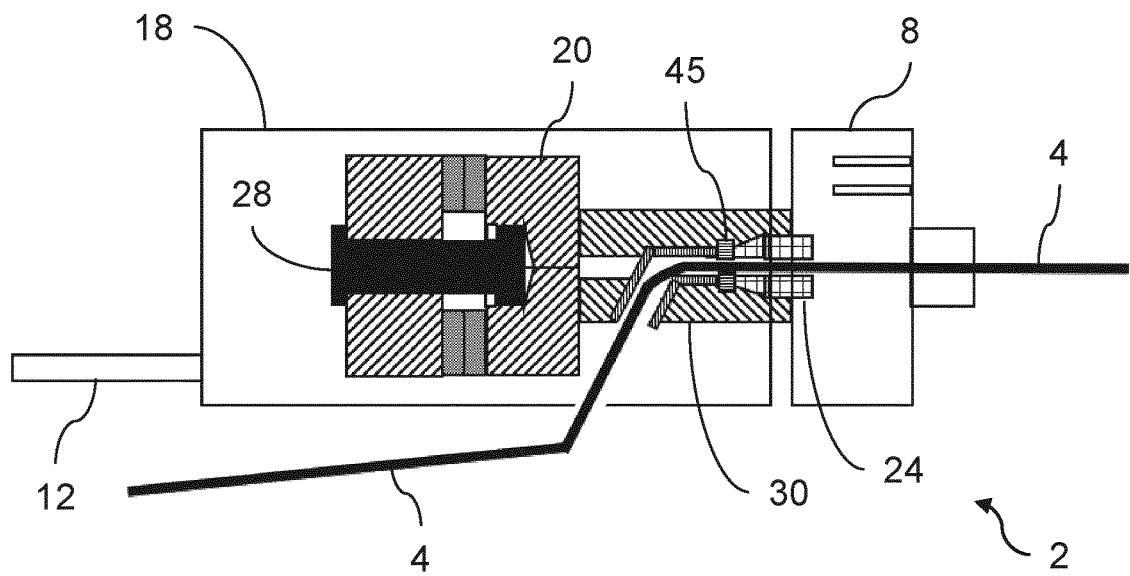
FIG. 4 corresponds to FIG. 2 but shows lateral exit of a guidewire from the transducer of the unit.

FIG. 4 shows a configuration similar to FIG. 2 but in this case the wire 4 does not traverse centrally through the entire length of the ultrasonic transducer 20. Instead, the wire 4 emerges laterally from the transducer 20 at a location between the piezoceramic stack 28 and the distal end or front mass 30 of the transducer 20 where the collet 24 is located.

Figure 5:
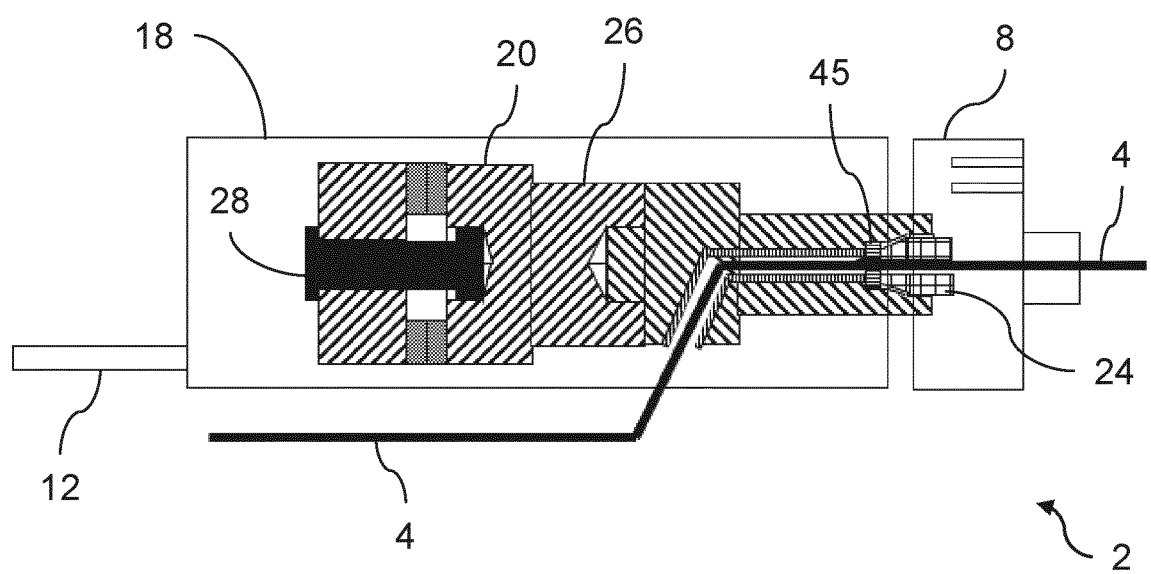
FIG. 5 corresponds to FIG. 4 but shows an acoustic horn coupled to a transducer within a housing of the unit.

Correspondingly, FIG. 5 shows a configuration similar to FIG. 3 but in this case the wire 4 does not traverse centrally through the entire ultrasonic transducer 20 and horn 26 but instead emerges laterally from the horn 26 at a location along the length of the horn 26, between the collet 24 and the distal face of the transducer 20. Thus, in FIGS. 4 and 5, the wire 4 deflects through an acute angle from the central longitudinal axis of the transducer 20 or of the horn 26 to exit laterally through a side of the transducer 20 or the horn 26.

It will be noted that the arrangements of the invention exemplified in FIGS. 2 to 5 differ from prior art that drives vibration of a wire using an electric motor and a cam or spindle to convert rotary motion to linear motion. Instead, the invention uses an ultrasonic transducer 20 that comprises a piezoceramic stack 28 and front and back (or distal and proximal) masses. This employs the piezoelectric effect of the piezoceramic stack 28, in which electrical energy is converted into high-frequency axial linear oscillation.

Additionally, unlike the prior art, the invention allows the wire 4 to extend through the activation unit 2 and yet to be coupled to the distal end of the transducer 20, which expression includes an acoustic horn 26 that may optionally be coupled to the distal end of the transducer 20. The prior art makes no provision, when using an ultrasonic transducer, to allow the wire to travel centrally through at least a distal end of the transducer. This feature of the invention allows the activation unit 2 to be moved along the wire 4 and then to be coupled to transmit ultrasonic energy to the wire 4 at any of a plurality of longitudinally-spaced locations along the wire 4.

Figure 6:
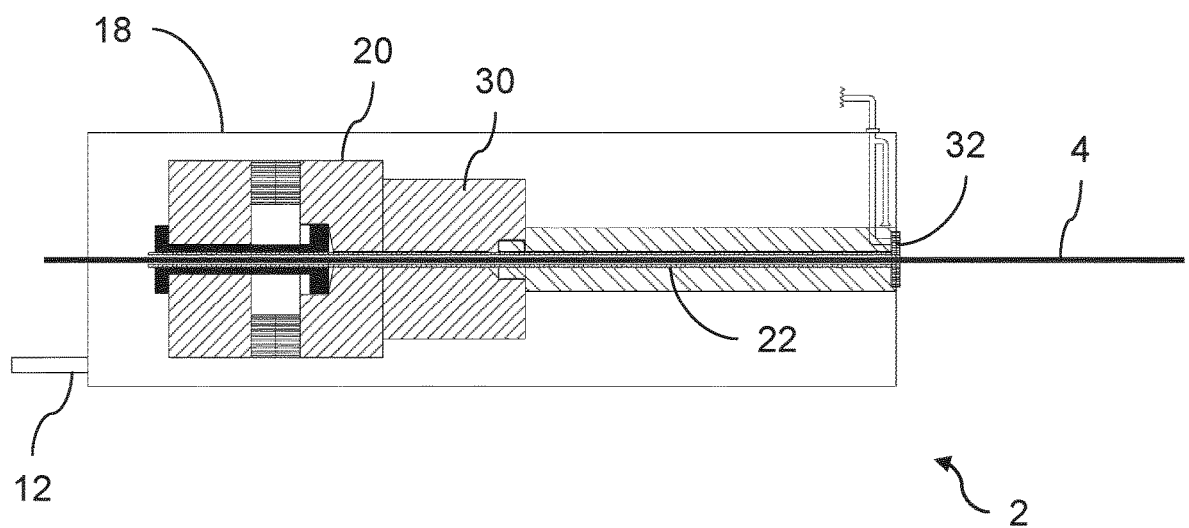
FIG. 6 is a schematic view in longitudinal section of a variant of the ultrasonic activation unit shown in FIG. 1, with clamping operable by pneumatic actuation.

FIG. 6 shows an activation unit 2 that, like the arrangement shown in FIG. 2, contains an ultrasonic transducer 20 that has a central lumen 22 to allow for the straight through-passage of the wire 4. In this case, however, the distal end of the transducer comprises a pneumatic micro-chuck 32 to allow for the engagement and release of the wire 4. The chuck 32 has angularly spaced jaws, for example three or four jaws, that act on the wire 4 directly, or via a collet 24, to clamp and release the wire 4 with constant force.

Specifically, pneumatic activation of the chuck system compresses the chuck 32 onto the wire 4, or onto a collet 24 disposed around the wire 4, to clamp the wire 4 at a pressure required to couple the ultrasonic energy emanating from the transducer 20. Air line pressure may be used to regulate the force applied by the chuck 32 so as to apply a constant required grip force. A solenoid may be used to control the capture and release of the wire 4 to allow the wire 4 to be moved or indexed longitudinally relative to the activation unit 2. This allows locking of the wire 4 in situ and overcomes possible variability in regulated air pressure.

In this example, a compressed air delivery port that communicates with the chuck branches to define a secondary channel. The secondary channel provides cooling airflow to cool the activation mechanism 2 in general and the coupling region in particular.

It will be apparent that the principle of the pneumatic chuck 32 shown in FIG. 6 can also be applied to arrangements that employ an acoustic horn 26 or in which the wire 4 exits the transducer 20 or horn 26 laterally, like those shown in FIGS. 3 to 5. For brevity, it should be noted that references to the transducer 20 in this description may refer to a front or distal mass 30 of the transducer 20 or to an acoustic horn 26 that is attached to a distal face of the transducer, hence effectively becoming an integral part of the transducer 20.

Figure 7:
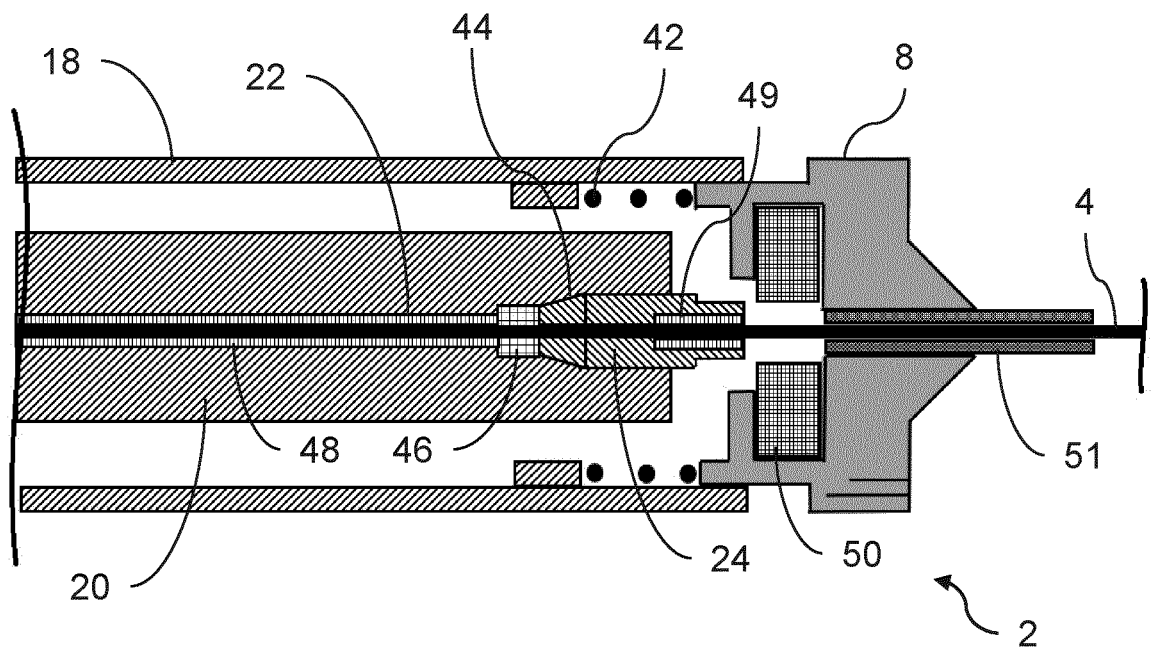
FIG. 7 is a schematic view in longitudinal section of an ultrasonic activation unit of the invention, in which an ultrasound-to-wire connector and coupling mechanism comprises a collet and a spring-loaded cap to apply torque.

Turning next to FIG. 7 of the drawings, the housing 18 of the activation unit 2 is tubular and surrounds the front mass of an ultrasonic transducer 20 coaxially. The transducer 20 extends distally to near the distal end of the housing. In this example, the wire 4 extends axially along and through the transducer 20 via a central lumen 22 but the wire 4 could instead exit the housing 18 laterally as in FIGS. 4 and 5. Also, the front mass of the transducer 20 could be substituted by an acoustic horn 26 as in FIGS. 3 and 5.

The distal end of the housing 18 is closed by the toggle 8. The toggle 8 can be turned about the central longitudinal axis of the wire 4 and can also be pushed axially in a proximal direction against distal bias of a spring 42 within the housing 18. The spring 42 may be a discrete spring such as a coil spring or may be formed by resilient formations such as spiral members that are attached to or integral with the housing 18 and/or with the toggle 8. The toggle 8 is shown here in a distal position biased by the spring 42 away from the distal end of the transducer 20. More generally, rotational and/or axial movement of the toggle 8 relative to the collet 24 may be guided or determined by a cam or spline formation.

A distally-opening, proximally-tapering socket or recess 44 in the distal end of the transducer 20 contains a proximally-tapering collet 24 that surrounds the wire 4 in alignment with the lumen 22 of the transducer 20. The collet 24 has a male thread that is engaged with a complementary female thread in the distal recess of the transducer 20.

The collet 24 is screwed into the recess of the transducer 20 and is then released by a user manipulating the toggle 8. Specifically, the user first pushes the toggle 8 axially in the proximal direction to engage the collet 24 and then turns the toggle 8 to advance the collet 24 proximally along the screw thread within the recess, hence to couple the transducer 20 with the wire 4 via the collet 24. When released by the user, the toggle 8 springs back distally and so disengages from the collet 24 so as not to interfere with transmission of ultrasound energy from the transducer 20 along the wire 4.

For this purpose, a distal end portion of the collet 24 protrudes distally from the distal end of the transducer 20. When the toggle 8 is pushed proximally against the bias of the spring 42, the toggle 8 engages the protruding distal end portion of the collet 24 via complementary interface formations. This engagement between the toggle 8 and the collet 24 allows torque to be transmitted from the toggle 8 to the collet 24, hence advancing the collet 24 proximally along the screw thread within the recess.

When the collet 24 is screwed into the recess of the transducer 20 in this way, the complementary proximally-tapering faces of the collet and the recess cause the collet 24 to clamp down on the wire 4 in a manner that distributes the clamping force along the wire 4 and avoids point loading. This clamping method in conjunction with an appropriate choice of the material of the collet 24 allows for excellent mating and ultrasonic transmission. The entire assembly of the transducer 20 and the collet 24 is tuned for optimal resonant response.

When the wire 4 is to be released from the activation unit 2, the collet 24 can be released by again pressing the toggle 8 proximally into engagement with the collet 24 and then turning the toggle 8 in the opposite direction to retract the collet 24 distally back along the screw thread in the recess of the transducer 20. This relaxes the grip of the collet 24 on the wire 4, allowing the wire 4 to be withdrawn from the activation unit 2.

Optionally, as shown in FIG. 7, an inner damper 46 may be disposed at a proximal end of the collet 24. This damper 46 is similar in function to the dampening ring 45 shown in FIGS. 2 to 5. In this example, the inner damper 46 is an annular collar of a hyperelastic material that surrounds the wire 4 in the lumen 22 of the transducer 20. When the collet 24 is screwed into the distal recess of the transducer 20, the damper 46 is compressed axially and thickens radially, hence being deformed around and pressing against the wire 4. The damper 46 thereby dampens or attenuates proximal transmission of ultrasonic energy imparted by the transducer 20 to the wire 4 via the collet 24.

FIG. 7 also shows an optional inner protective sleeve 48 disposed around the wire 4 within the lumen 22. The sleeve 48 is made of a low-friction, highly wear-resistant material to centre the wire 4 within the lumen 22 and to shield the wire 4 from the surrounding wall of the transducer 20. The sleeve 48 is preferably made of a material that, like the damper 46, has a damping or attenuating effect on the proximal transmission of ultrasonic energy imparted by the transducer 20 to the wire 4. Similar sleeves 49, 51 may be disposed in the distal portion of the collet 24 and in between the toggle 8 and the wire 4 to centre and support the wire 4 as it emerges distally from the collet 24. The sleeve 51 between the toggle 8 and the wire 4 may partly extend distally therefrom. Like the sleeve 48 provided between the transducer 20 and the wire 4, the sleeves 49, 51 provided in the collet 24 and the toggle 8 are preferably configured to have a damping or attenuating effect on the proximal transmission of ultrasonic energy imparted to the wire 4.

Another optional feature shown in FIG. 7 is a torque limiter 50 within the toggle 8 that, when the toggle 8 is engaged with the collet 24, acts between the exterior of the toggle 8 and the collet 24. The torque limiter 50 causes the toggle 8 to slip relative to the collet 24, for example by deformation of flexible or resilient interface formations of the toggle 8 and/or the collet 24, if torque applied to the toggle 8 by a user exceeds a predetermined limit. This prevents the user over-tightening the collet 24 by applying too much torque to the toggle 8, which could otherwise cause the collet 24 to overcompress and hence over-stress and risk failure of the wire 4.

The toggle 8 shown in FIG. 7 also includes a strain-relief feature that is exemplified here by a distally-tapering formation around the wire. This feature mitigates kinking and possible over-stressing of the wire 4 where the wire 4 emerges through the toggle 8 from the housing 18 of the activation unit 2.

Figure 8:
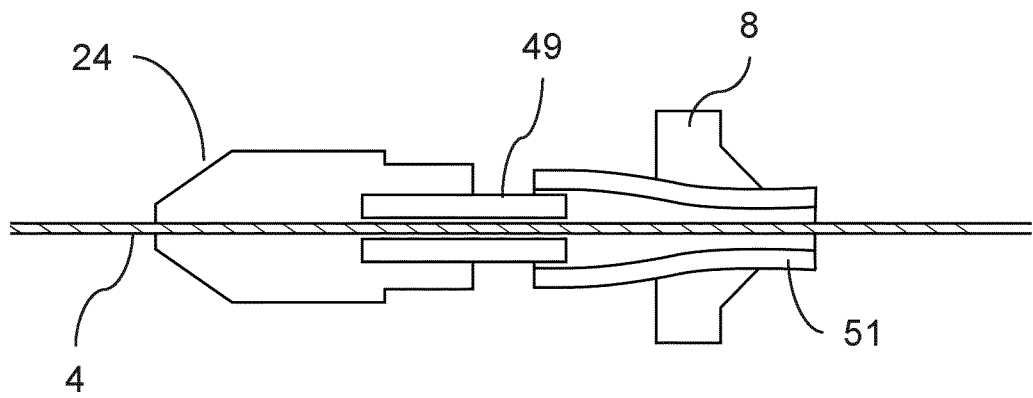
FIG. 8 shows an alternative configuration for a distal damper shown in FIG. 7.

FIG. 8 shows an alternative configuration for two of the distal dampers shown in FIG. 7. Here, the collet-based wire sleeve 49 partially extends distally from the collet 24 and the toggle-based wire sleeve 51 extends proximally from the toggle 8. The toggle-based wire sleeve 51 may extend distally from the toggle 8 too. The proximal end of the toggle-based wire sleeve 51 encloses, and preferably clamps, the distal end of the collet-based wire sleeve 49, such that a continuous connection between the two is obtained and the distal damping characteristics of the activation unit 2 are further improved. Alternatively, the distal end of the collet-based wire sleeve 49 may be configured to enclose the proximal end of the toggle-based wire sleeve 51, with similar effect.

Figure 9:
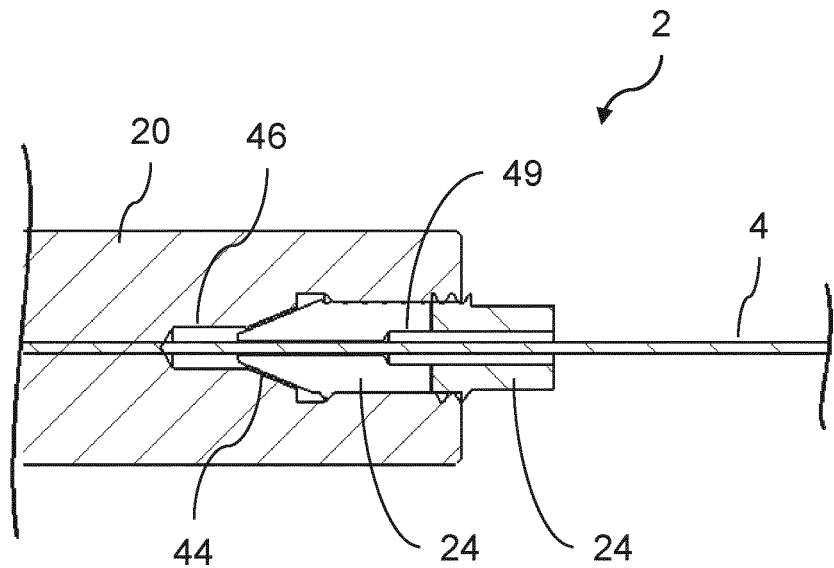
FIG. 9 shows a single-tapered collet inside a distal recess of the transducer, with proximal and distal damping.
Figure 10:
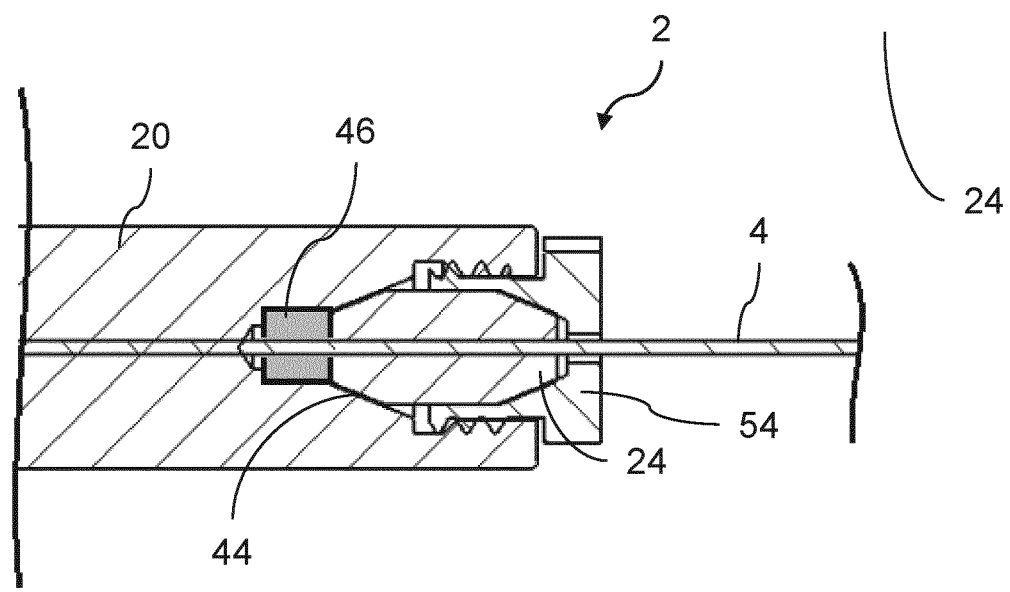
FIG. 10 shows a double-tapered collet inside a distal recess of the transducer, with proximal damping.

FIG. 9 shows a single-tapered collet 24 in which only the proximal end of the collet 24 is tapered to seat into a complementary taper at the base of a distal recess 44 of the transducer 20. Conversely, FIG. 10 shows a double-tapered collet 24 in which the distal end of the collet 24 also tapers distally.

The primary objective of the collets 24 used in the invention is to achieve excellent acoustic coupling between the wire 4 and the rest of the system. In this respect, the transducer 20 and the coupling method have to work in unison. In particular, the transducer 20, with coupling interface components optionally including an acoustic horn, is designed to resonate at the driving frequency of the system.

The shape and dimensions of the transducer 20 are chosen to achieve an amplification gain while ensuring that the system remains near to its operating resonant frequency. In addition, any modifications to a distal driving face of the transducer 20 so as to accommodate a connector have to be considered and accounted for with regard to resonant response.

FIG. 9 shows a transducer 20 fitted with a single-taper male-threaded collet 24. The collet 24 anchors the wire 4 within a complementary threaded bore or recess 44 in the distal end of the transducer 20 when torque is applied to the collet 24 to advance the collet 24 into the recess 44. A complementary taper at the proximal base of the recess 44 then compresses the collet 24 radially to grip the wire 4. When the collet 24 is advanced fully into the recess 44 as shown in FIG. 4, a distal end portion of the collet 24 is left protruding distally from the distal end of the transducer 20. A damper 46 at the proximal end of the recess 44 and a damping sleeve 48 similar to the collet-based sleeve 48 shown in FIG. 7 are provided for damping or attenuating proximal transmission of ultrasonic energy imparted by the transducer 20 to the wire 4.

FIG. 10 shows a transducer 20 fitted with a double-taper collet 24 and a cap screw 54. The proximal taper of the collet 24 is received in a countersunk distal recess 44 in the distal end face of the transducer 20. The cap screw 54 similarly receives and complements the taper at the distal end of the collet 24. Torque applied to the cap screw 54 advances the cap screw 54 to compress the collet 24 longitudinally and to compress the collet 24 radially to grip the wire 4.

Like the arrangement shown in FIG. 7, an internal damper 46 is disposed within the transducer 20 at a proximal end of the collet 24. The damper 46 is an annular collar of a hyperelastic material that surrounds the wire 4 in the lumen 22 of the transducer 20. When the collet 24 is forced proximally into the distal recess 44 of the transducer 20, the damper 46 is compressed axially and thickens radially, hence being deformed around and pressing against the wire 4. The damper 46 thereby dampens or attenuates proximal transmission of ultrasonic energy imparted by the transducer 20 to the wire 4 via the collet 24. In this arrangement, and that of FIG. 7, a plurality of dampers 46 or one longer damper 46 could be deployed over a length within the transducer body 20.

Figure 11:
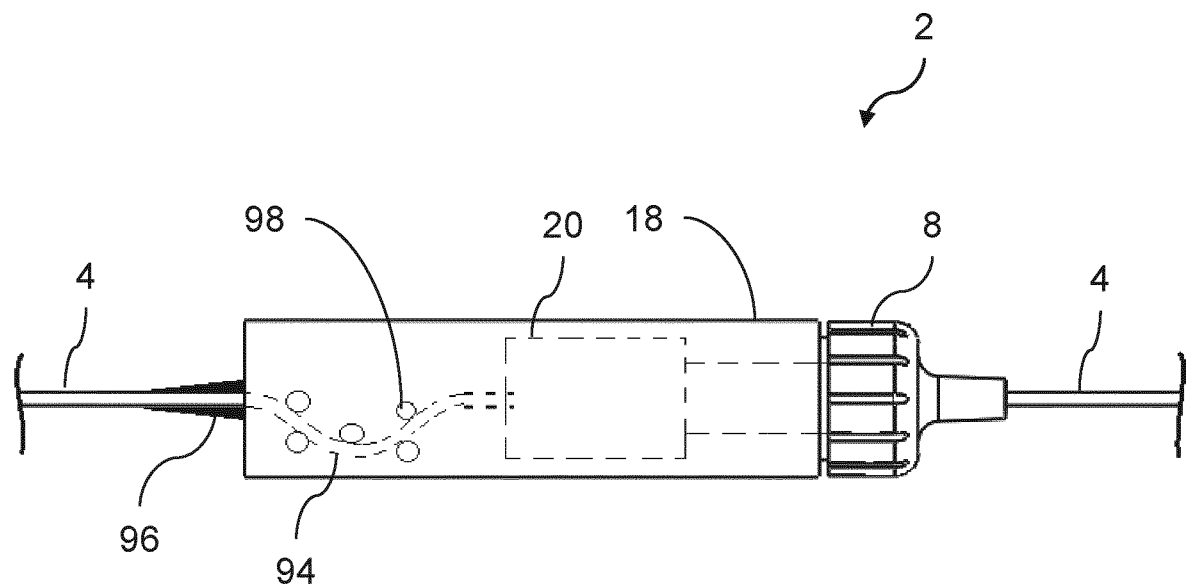
FIG. 11 is a longitudinal sectional view of a hand-held ultrasonic activation unit showing internal features within its housing for damping the proximal wire.

FIG. 11 shows internal damping features within the housing 18 of the activation unit 2, in which the portion of the wire 4 emerging proximally from the transducer 20 passes through a tortuous series of bends 94. Guiding the wire 4 through these convoluted bends 94 attenuates the ultrasound energy and therefore reduces proximal transmission. The proximal portion of the wire 4 may also extend through a tube 96 with a high coefficient of friction. In that case, the effect of the bends 94 increases frictional forces between the wire 4 and the surrounding tube 96, resulting in further attenuation of the ultrasonic energy. Friction also arises between the wire 4 and the features such as transverse pins 98 that define the bends 94.

Figure 12:
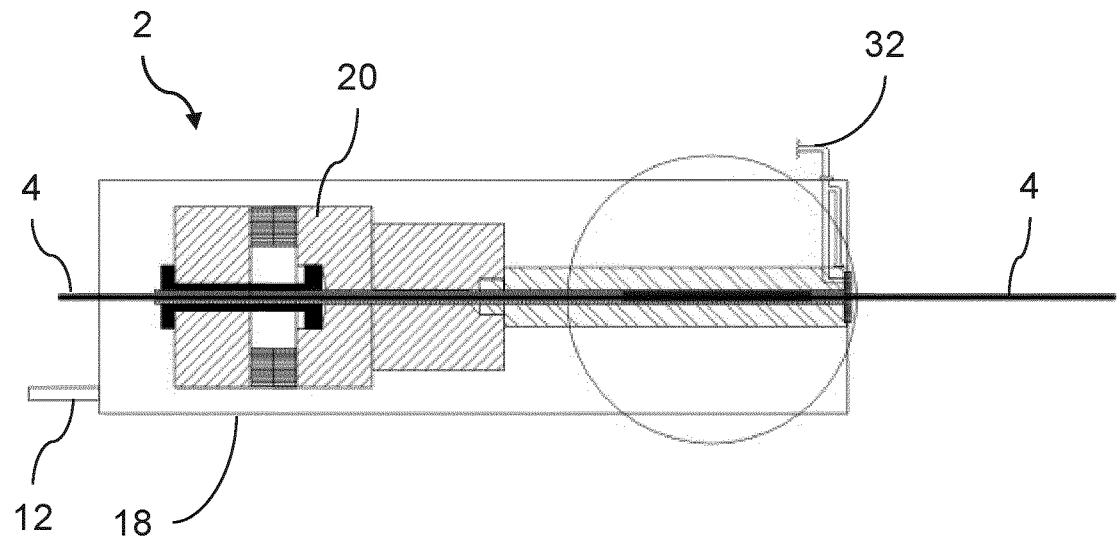
FIG. 12 is a longitudinal sectional view of a hand-held ultrasonic activation unit comprising a medium to negate proximal wire activity.
Figure 13:
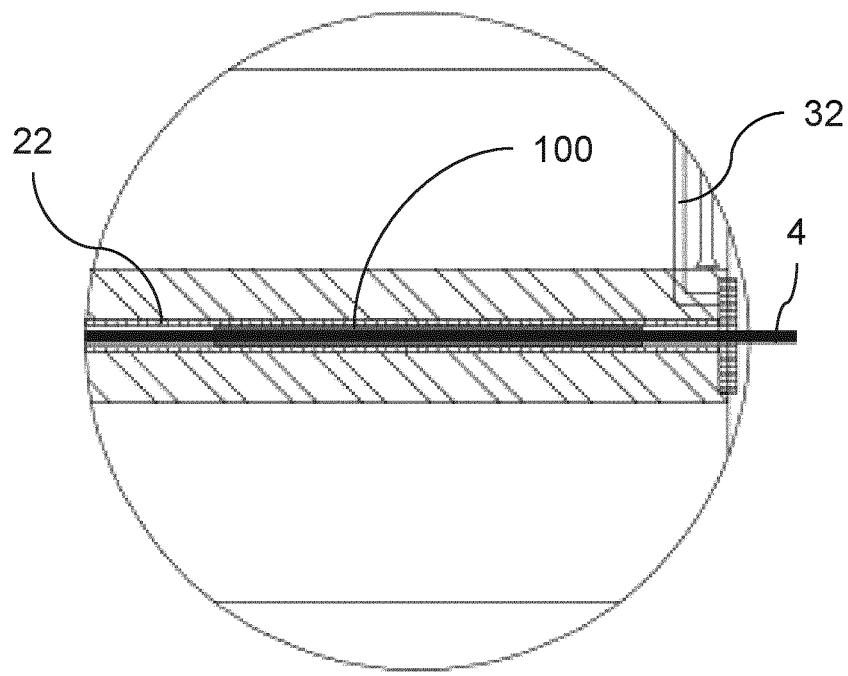
FIG. 13 is an enlarged view showing a detail of FIG. 12.

In addition, the proximal portion of the wire 4 may be slid through hyperelastic tubing, such as of silicone, that has an inner diameter equal to or less than the outer diameter of the wire. To exemplify this former possibility, FIGS. 12 and 13 correspond to the pneumatically-clamped arrangement of FIG. 6 but show a damping medium 100 disposed around the wire on the proximal side of the pneumatic micro-chuck 32.

Figure 14:
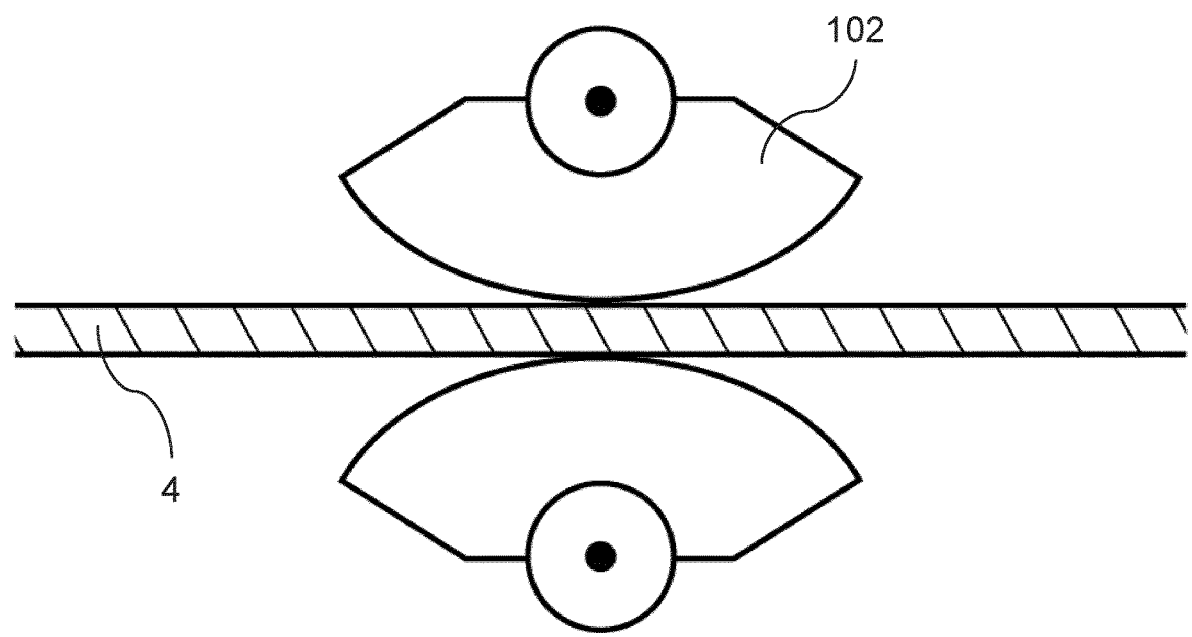
FIG. 14 is an end view of a cam arrangement for engaging and damping the wire.
Figure 15:
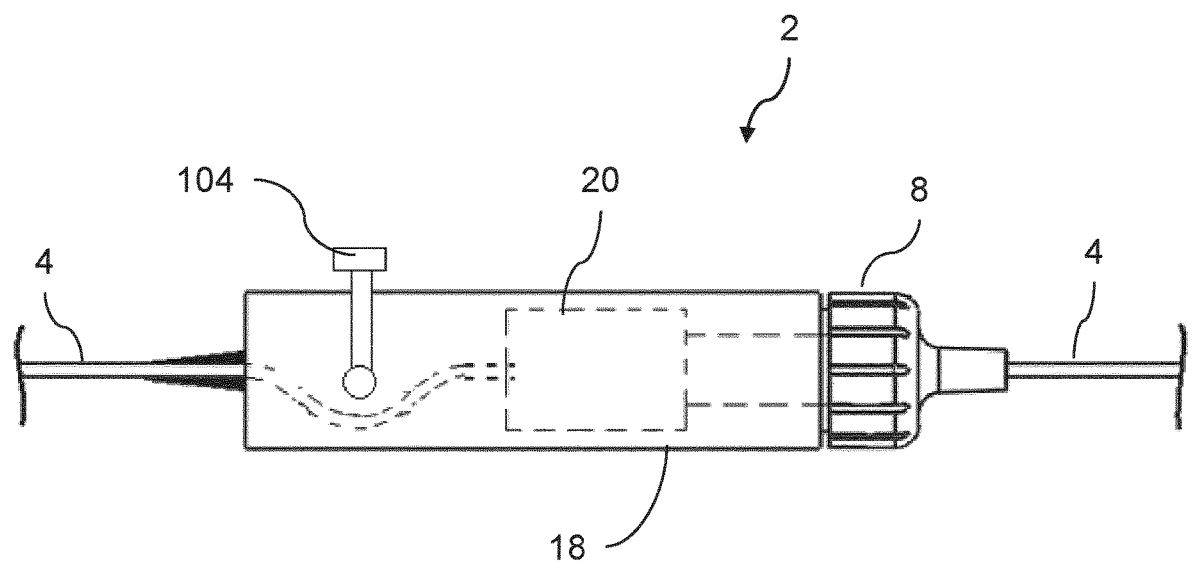
FIG. 15 is a longitudinal sectional view of a hand-held ultrasonic activation unit comprising a push-button wire damping mechanism.

Also, the proximal portion of the wire 4 may be actively clamped or bent off centre by means of a mechanism that is either independent of, or linked to, the main user toggle 8. For example, FIG. 14 shows how the proximal portion of the wire 4 can be captured between offset cams 102 within the activation unit 2. FIG. 15 shows a push-button damping mechanism 104 that can be pressed radially-inwardly against the proximal portion of the wire 4 within the activation unit 2. The push-button damping mechanism 104 is configured to put pressure on the wire 4 and so dampen displacement of the wire 4.

Figure 16A:
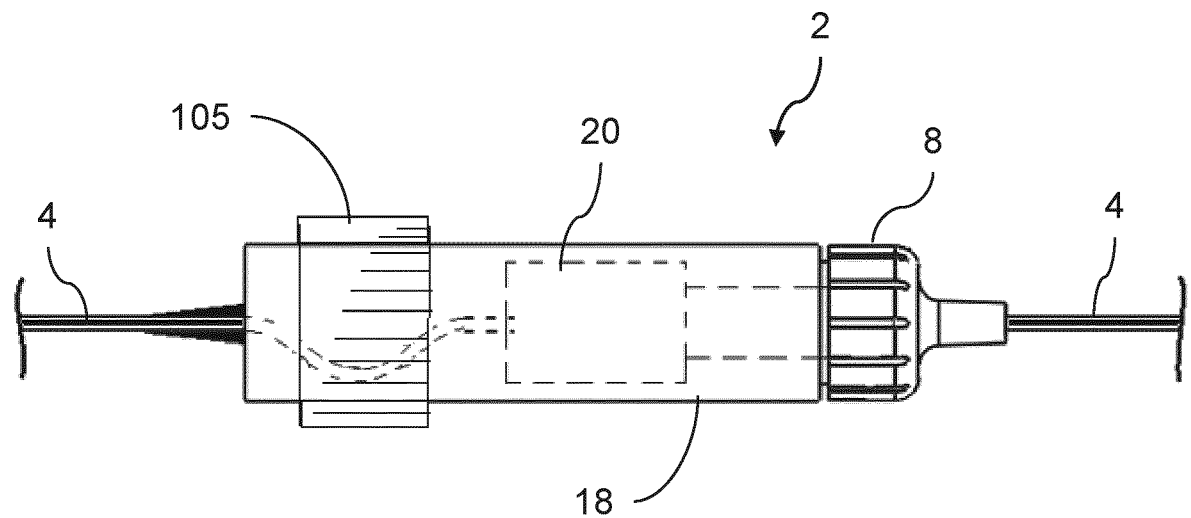
FIG. 16a is a longitudinal sectional view of a hand-held ultrasonic activation unit comprising a spiral wire damping mechanism.
Figure 16B:
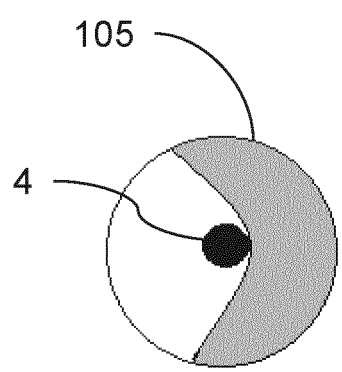

In FIG. 16a, the housing 18 of the activation unit 2 is fitted with a damping mechanism 105 at its proximal end comprising a proximal cap that can be turned to bring a laterally-offset spiral formation into damping contact with the proximal portion of the wire 4. FIG. 16b shows a cross-sectional view through the damping mechanism 105.

It will be noted in FIGS. 15 and 16a that the proximal portion of the wire 4 is surrounding by a strain relief feature, extending proximally from the housing 18, that also effects lateral damping of the wire 4.

Figure 17:
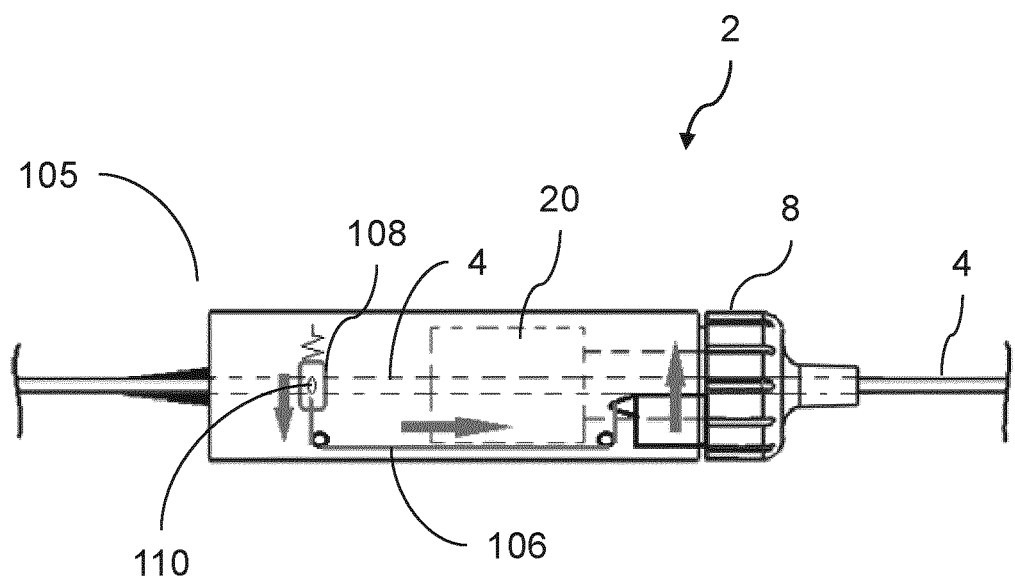
FIG. 17 is a longitudinal sectional view of a hand-held ultrasonic activation unit comprising another wire damping mechanism.

FIG. 17 exemplifies how modulation of proximal vibration may be achieved automatically by a user turning a distal toggle 8. As the toggle 8 is turned, a guide cable 106 within the housing of the activation unit 2 is displaced. This pulls a spring-loaded element 108 that acts on the proximal portion of the wire 4 via a friction collar 110 through which that portion of the wire 4 extends. By increasing frictional forces on the wire 4 and constraining its vibration, this attenuates the ultrasound energy that would otherwise be directed proximally from the activation unit 2. In other embodiments, the friction collar 110 may be controlled electronically. A similar distal toggle 8 may then be used for adjusting the friction force via an electronic coupling between the distal toggle 8 and the friction collar 10.

Figure 18:
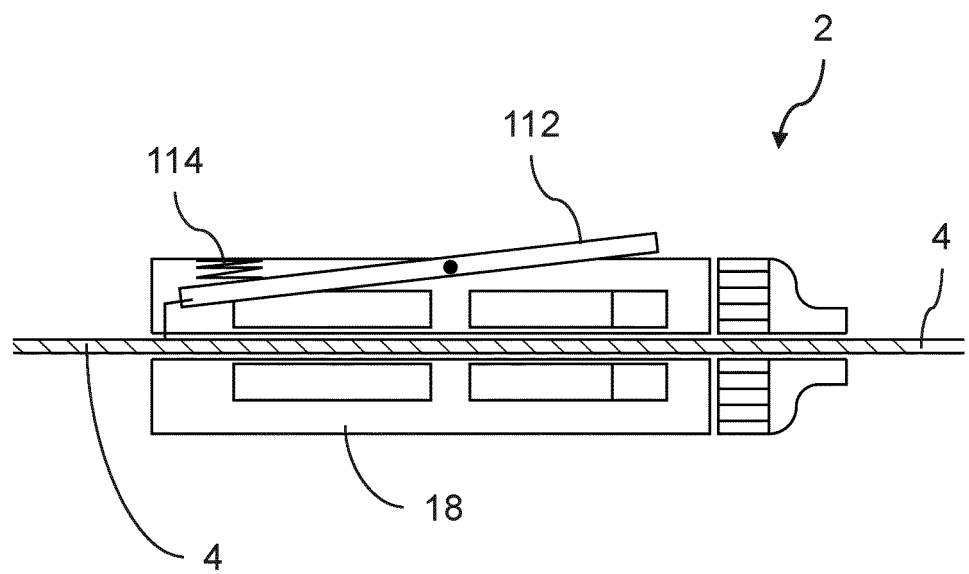
FIG. 18 is a longitudinal sectional view of a hand-held ultrasonic activation unit comprising another wire damping mechanism, which can be disengaged as required to allow for the repositioning of the wire.

FIG. 18 shows another way in which the proximal portion of the wire 4 may be clamped to damp ultrasonic oscillation. Here, the housing 18 of the activation unit 2 supports a lever 112 that extends longitudinally along the housing 18. The proximal end of the lever 112 is biased by a spring 114 into damping contact with the proximal portion of the wire 4. When it is desired to remove the wire 4 from the activation unit 2, the distal end of the lever 112 can be depressed to release the pressure applied by the lever 112 to the proximal portion of the wire 4.

Figure 19:
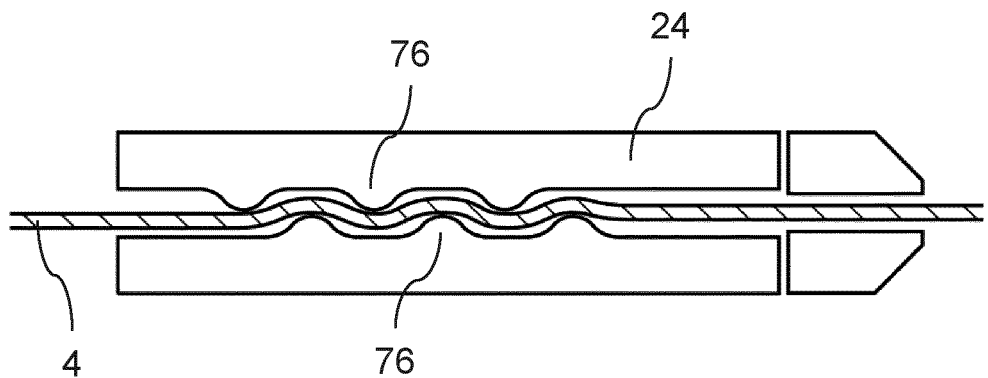
FIG. 19 is a side view of a longitudinally split collet arranged to damp proximal excitation of the wire.

Damping features can also be incorporated in a collet 24. For example, FIG. 19 shows a split collet 24, in which the proximal portion of the wire 4 is forced into a serpentine path defined by opposed guide formations 76 in the confronting faces of the collet 24. Specifically, longitudinally-staggered projections 76 alternate between the opposed parts of the collet 24 to define an undulating path between them. The projections 76 may be made of a compliant material to damp excitation effectively.

Figure 20:
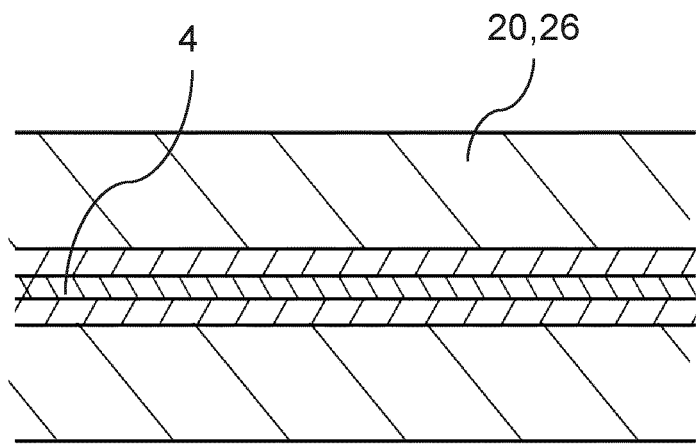
FIG. 20 is a schematic view of a wire showing examples of attachment location markers.
Figure 21:
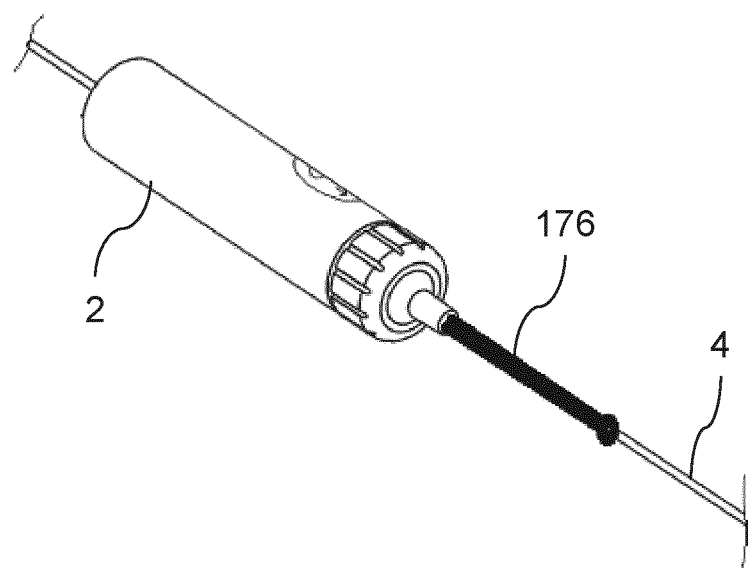
FIG. 21 is a perspective view of an ultrasonic activation unit of the invention, fitted with a detachable distal safety and strain relief feature.

FIG. 20 shows how the inner lumen of a transducer or horn may be injected with a foam or resilient polymer material to negate activity in the proximal portion of the wire extending proximally from the coupling and from the activation unit.

Turning next to FIGS. 21 to 24, these drawings show a safety feature in which a rigid tube 176 protruding distally from the distal end of the activation unit 2 surrounds and ensheaths the distal portion of the wire 4. The main purpose of the tube 176 is to prevent the handheld activation unit 2 being advanced so far distally toward a patient during a procedure that there could be a risk of the wire 4 being lost within the patient's body if the wire 4 breaks. The tube 176 has a secondary benefit of providing strain relief and lateral damping to the distal portion of the wire 4.

Figure 22:
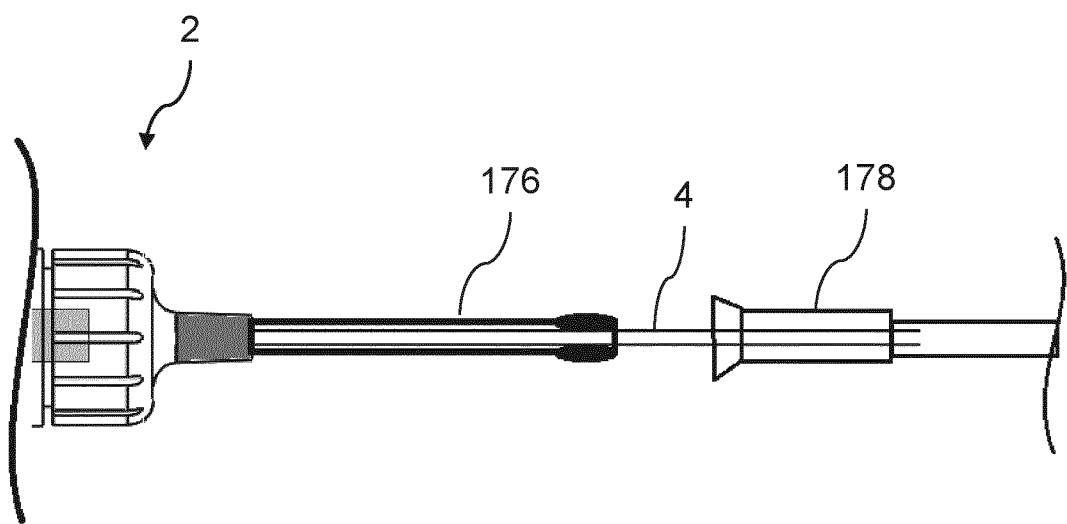
FIG. 22 is a longitudinal sectional view of the arrangement of FIG. 21 in use during a procedure.

In particular, as shown in FIG. 22, the tube 176 acts as a spacer that prevents a user advancing the activation unit 2 all the way to a catheter entry port 178, commonly referred to in the art as a 'luer'. The length of the tube 176 imposes a standoff distance between the activation unit 2 and the entry port 178. The distal end of the tube 176 may be bulbous or otherwise enlarged, as shown, to serve as an end stop or insertion limiter that prevents the tube entering the entry port.

The length of the tube 176 ensures that a section of the wire 4 will always remain outside the patient's body even if the wire 4 breaks. Specifically, if the wire 4 fractures near its point of coupling to the transducer 20 within the activation unit 2, a length of wire 4 at least as long as the tube 176, and typically somewhat longer than the tube 176, will always remain outside the entry port 178. In this case, friction between the wire 4 and the tube 176 will help to prevent the wire 4 slipping distally along the tube 176 and into the patient's body.

Figure 23:
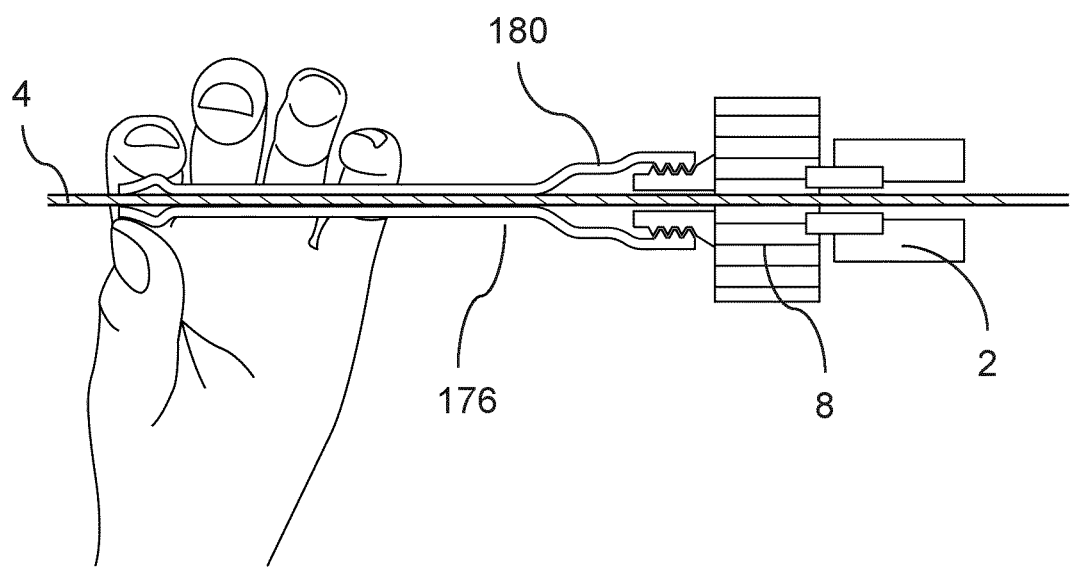
FIG. 23 is a perspective view that shows the arrangement of FIG. 21 in use during a procedure.
Figure 24:
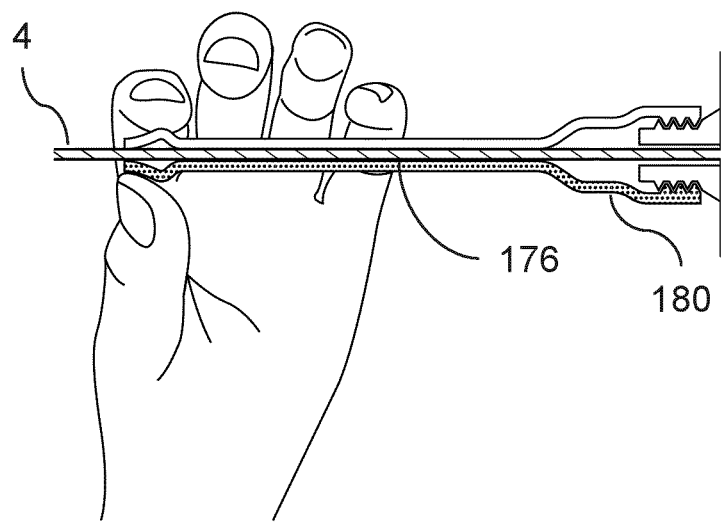
FIG. 24 is another perspective view that shows the arrangement of FIG. 21 in use during a procedure.

FIGS. 23 and 24 show that the tube 176 may have the further attribute of being radially compressible between a user's fingers so as to grip the wire 4 within the tube 176 in the event of breakage. This helps the user to prevent the broken end of the wire 4 being drawn into the patient's body. The tube 176 may be compressible in this way at its proximal end or at any point along its length but is preferably compressible at or near to its distal end as shown.

Advantageously, the tube 176 may also be detached easily from the activation unit 2 to allow quick access to the wire 4. For this purpose, the tube 176 is readily detachable from the distal end of the activation unit 2 by releasing a detachable connector 180 at the proximal end of the tube 176 from the distal side of the toggle 8. There, the tube 176 may, for example, be detached from the activation unit 2 by a twist-off or press/pull arrangement.

Thus, a user can squeeze the tube 176 to grip the fractured wire 4 and then, while still gripping the wire 4, can pull the tube 176 away from the activation unit 2 to ensure that the wire 4 remains outside the patient's body.

Figure 25:
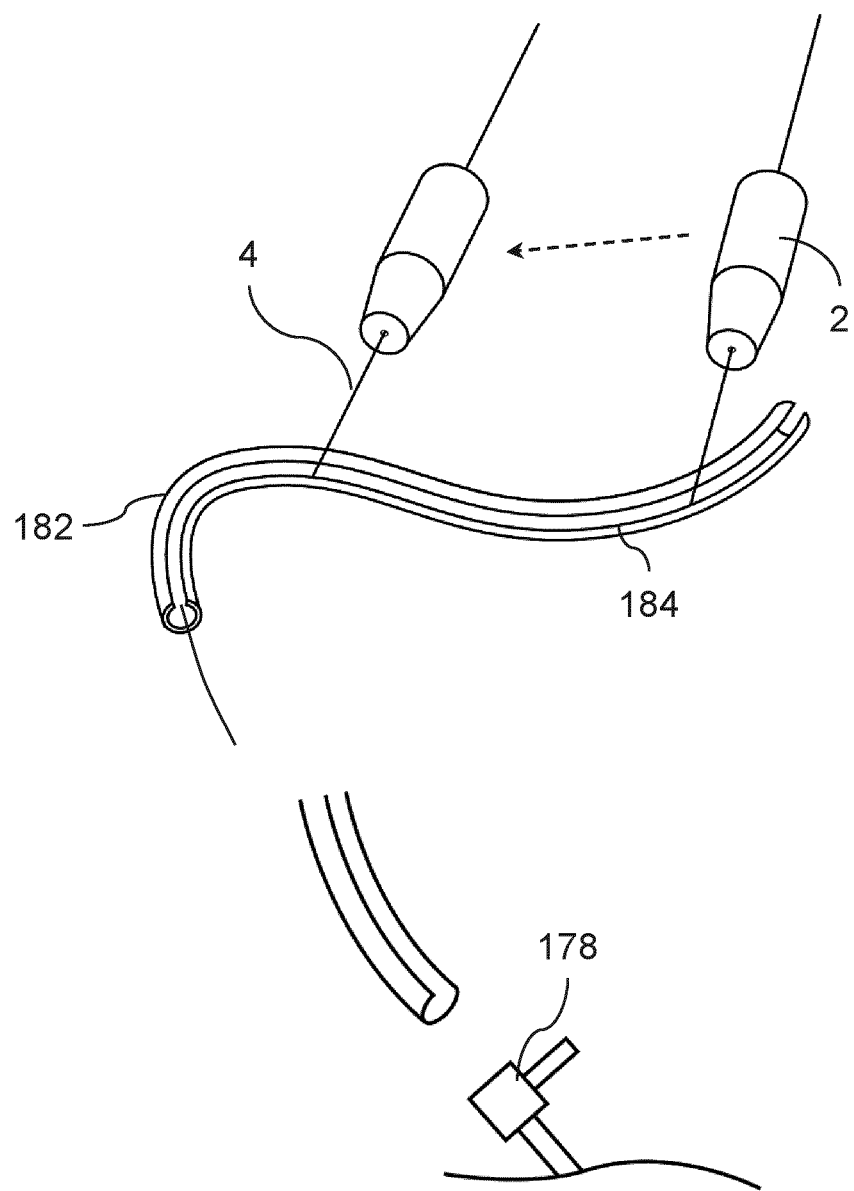
FIG. 25 is a schematic view of a protective sheath for use with the invention.

Moving on now to FIG. 25, this shows a flexible tubular protective catheter or sheath 182. At the outset of a procedure, the sheath 182 extends along and around the distal portion of the wire 4 extending between the activation unit 2 and the luer or introducer that defines an entry port 178 leading into the patient's body. The purpose of the sheath 182 is to surround and protect this length of wire 4, which would otherwise be exposed before being advanced into the patient's body. The wire 4 can pass easily through the loose sheath 182 while the sheath 182 prevents the wire 4 coming into contact with any materials that could contaminate the wire 4 or modify, and in particular damp, the oscillation of the wire 4.

The sheath 182 is particularly useful where a long wire 4 must be inserted into the patient's body, for example to cross a blockage in the distal tibial or pedal arteries. In particular, the tubing 182 helps such a substantial length of wire 4 to be inserted in a single continuous movement rather than intermittently in a succession of shorter movements, as would be the case if the activation unit 2 is instead repeatedly clamped to the wire 4 and released from the wire 4.

Thus, instead of being held close to the introducer 178, the activation unit 2 is coupled to the wire 4 at a location remote from the introducer 178 and so is ready for the full length of the wire 4 to be introduced into a target vessel. As a result, the user may simply clamp the activation unit 2 to the wire 4 at a proximal location a metre or more from the patient's body and then can activate and deliver a long section of the wire 4 into the body in a single uninterrupted action.

The sheath 182 must not hinder distal movement of the activation unit 2 and the wire 4 toward the introducer 178. Thus, the sheath 182 may collapse along its length or concertina as the activation unit 2 and the wire 4 are advanced distally. In another approach, as shown here, the sheath 182 has a longitudinal slit 184, groove zipper or other closure along its length to split longitudinally and then peel away from the wire 4 to provide clearance as the activation unit 2 and the wire 4 advance together distally through the sheath 182.

Figure 26:
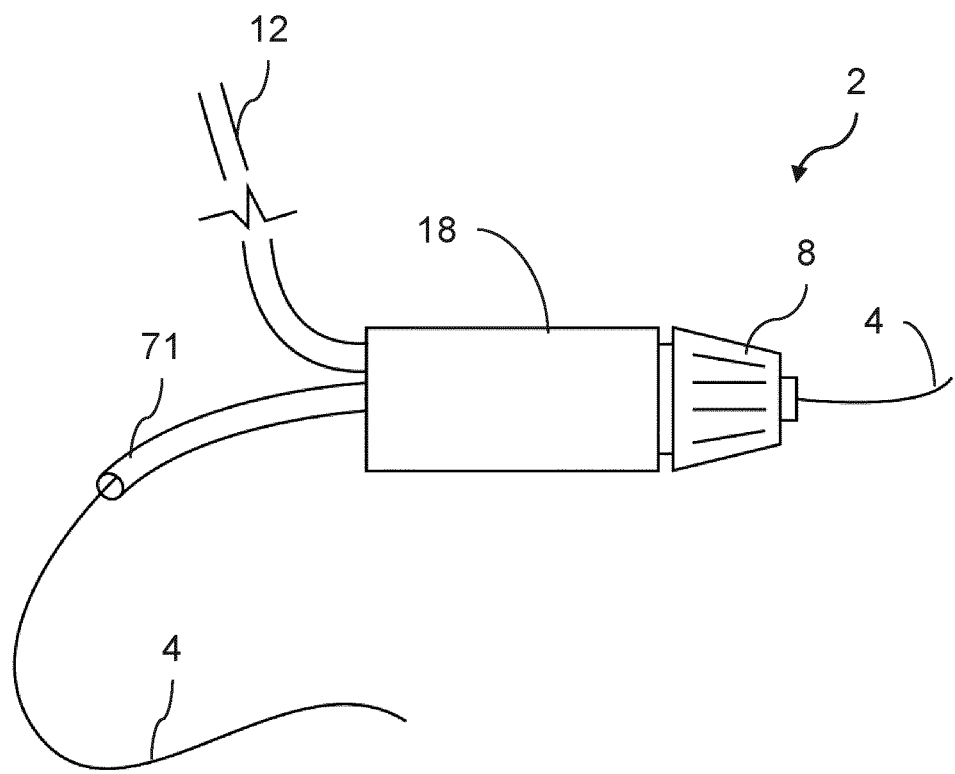
FIG. 26 shows an ultrasonic activation unit with proximal damping features.

In FIG. 26, displacement or movement of the proximal end of the wire 4 is reduced by a flexible tubular sleeve 71 that surrounds the proximal part of the wire 4, where it exits the housing 18 of the activation unit 2. This flexible tubular sleeve, e.g. made of an elastic polymeric material, bears against the wire 4 and thereby dampens its movements.

Figure 27:
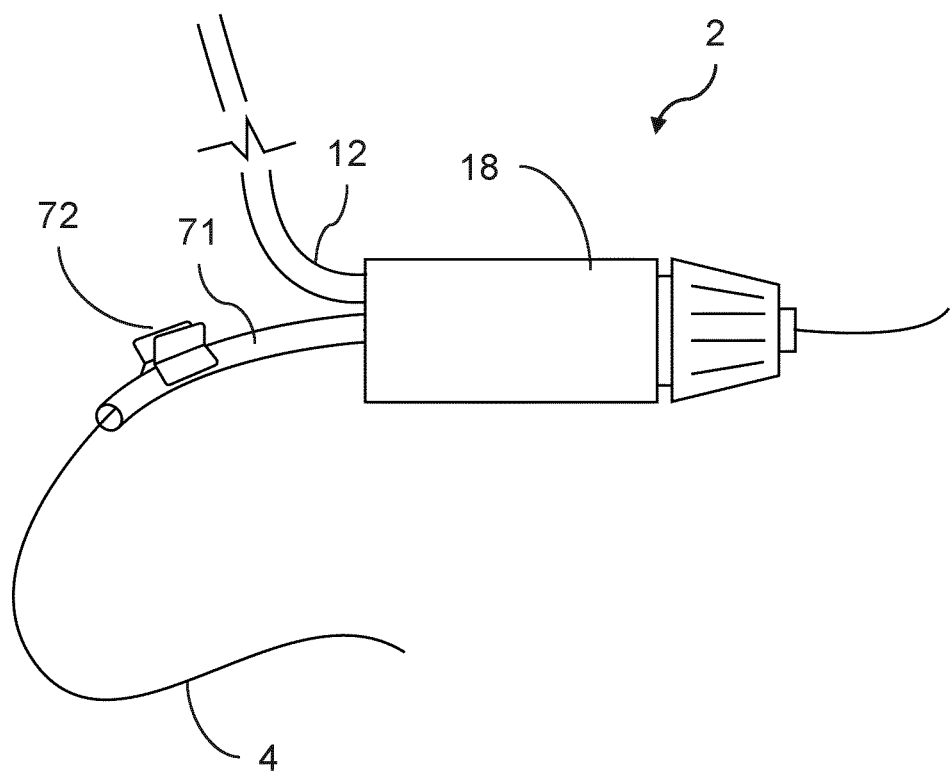
FIG. 27 shows another ultrasonic activation unit with proximal damping features.
Figure 28:
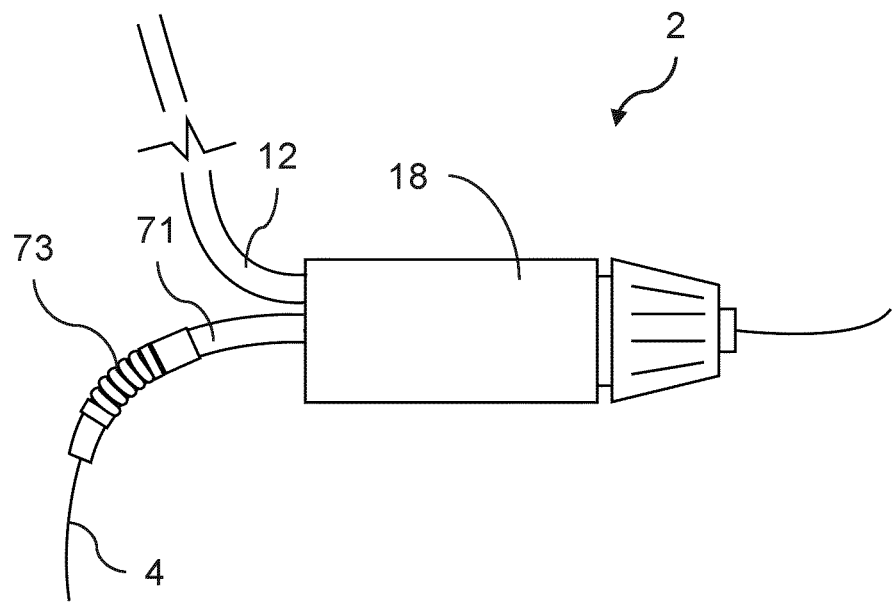
FIG. 28 shows yet another ultrasonic activation unit with proximal damping features.

FIG. 27 shows a similar embodiment of the activation unit 2. In addition to what is already shown in FIG. 26, this embodiment further comprises a clamp 72 that squeezes the flexible tubular sleeve 71 onto the wire 71. The clamp 72 may be movable longitudinally along the sleeve 71 to a position that results in the best damping effect. In FIG. 28, the clamp 72 is replaced by a collet 73 that can be moved along the sleeve 71 too. Additionally, the collet 73 may be adapted to control the clamping force with which it clamps the tubular sleeve 71 and the wire 4 extending therethrough. A double collet 73 provides a damping feature that compresses the wire in the axial or longitudinal direction and could clamp the wire 4 at more than one point. In further embodiments, the clamp 72 of FIG. 27 and the collet 73 of FIG. 28 could be combined.

Figure 29:
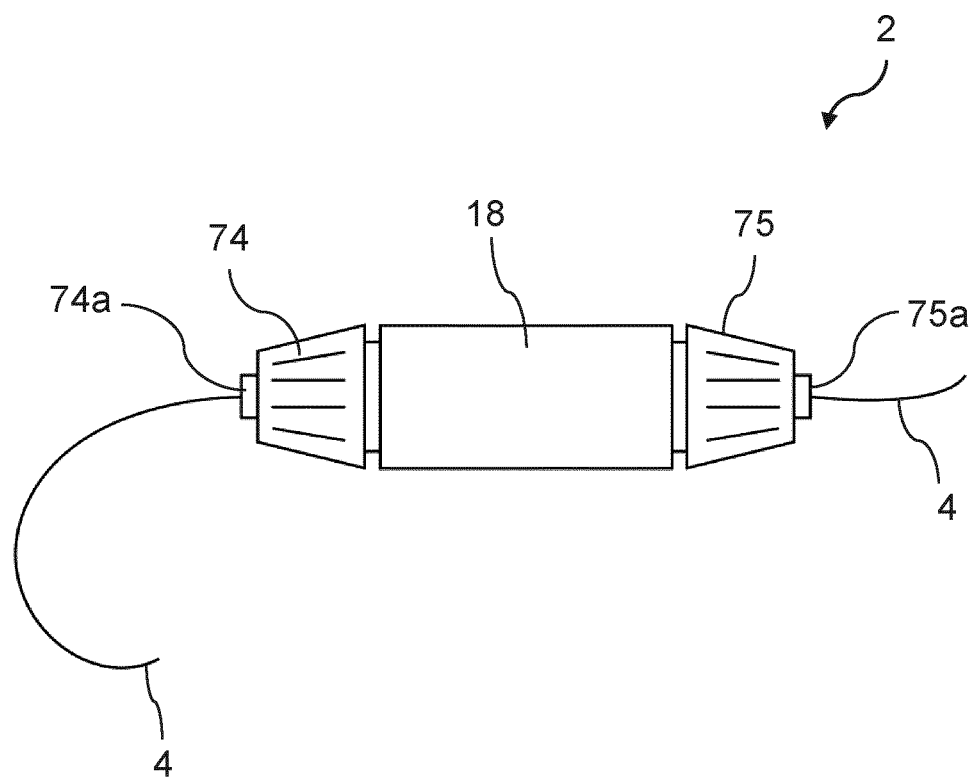
FIG. 29 shows an ultrasonic activation unit with proximal and distal twist-locks for clamping the endovascular wire at two points.

In FIG. 29, the activation unit 2 comprises a proximal twist-lock 74 that clamps onto the proximal part of the wire 4 and couples it to the housing 18 of the activation unit 2 for damping displacement or movement of the proximal portion of the wire 4. The proximal twist-lock 74 may comprise a collet 74a or tubular sleeve that surrounds the wire 4 and is tightened by operating the proximal twist-lock 74. In addition thereto, the activation unit 2 may comprise a similar distal twist-lock 75 with a collet 75a that couples the transducer to the distal part of the wire 4. Each or both of the twist-locks 74, 75, but preferably at least the distal twist-lock 75, may be combined with a user toggle 8 as disclosed FIG. 1 and many of the other Figures discussed above. Such a user toggle 8 will then be configured to be rotatable independently from the twist-lock 74, 75, around the same longitudinal axis. Another mechanism, or the operator, could place the wire 4 in tension or under compression before locking, or the wire 4 could be left neutral before locking.

Figure 30A:
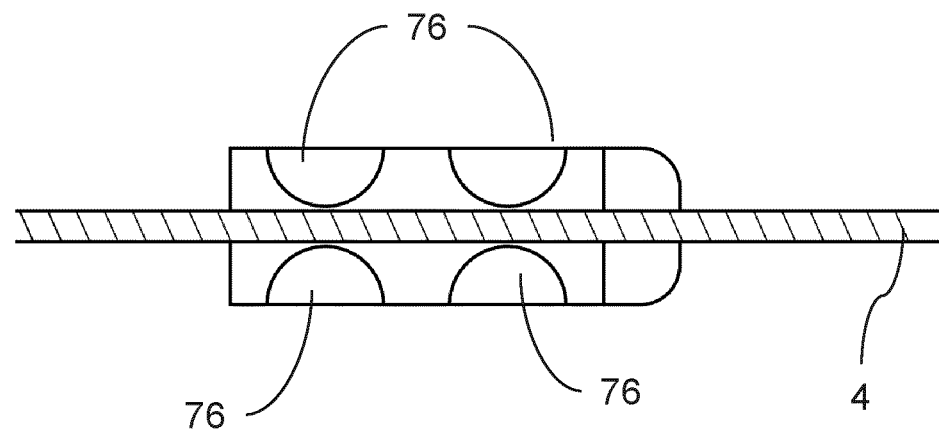
FIGS. 30a, 30b, and 30c show three arrangements of projections for reducing lateral movement of the endovascular wire.
Figure 30B:
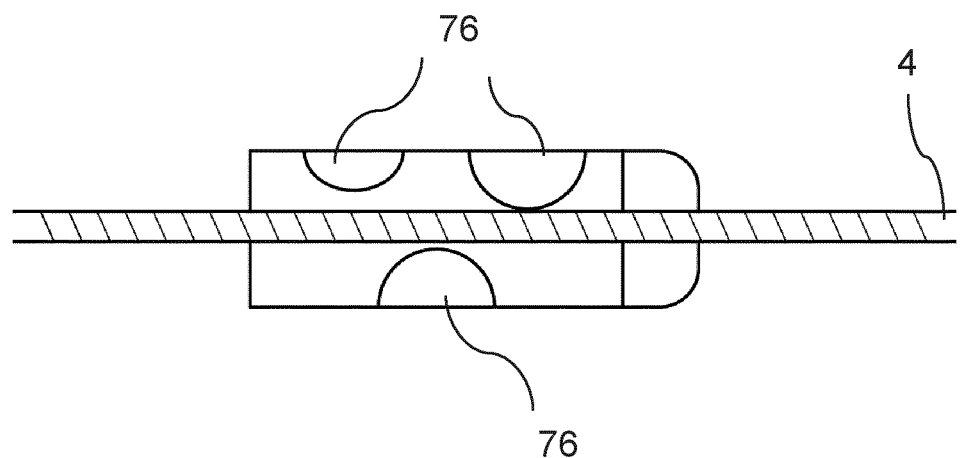
Figure 30C:
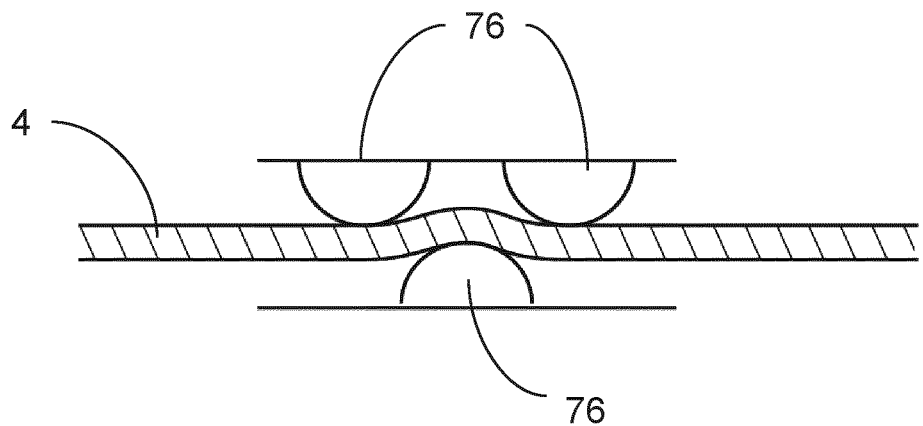

FIGS. 30a, 30b and 30c show three different arrangements of wire holding formations 76 that may be provided inside the housing 18 of the activation unit 2, preferably at least at its proximal end, in order to firmly hold the wire 4 and thereby attenuate the displacement or movement of its proximal portion. These wire holding formations 76 may, as already shown in FIG. 19, be provided inside a collet 24, or in any other element surrounding the wire 4 and rigidly installed inside the housing 18. The wire holding formations 76, which may be spring-biased, bear against, and damp vibration of, the proximal part of the wire 4. In FIG. 30a, four wire holding formations 76 together provide two contact points with the wire 4. In FIG. 30b, three wire holding formations 76 provide three contact points. In FIG. 30c, the three wire holding formations 76 are arranged such that the wire 4 adopts a sinuous path through the longitudinally-staggered contact points, similar to the path shown in FIG. 19. Combinations and variations of the arrangements shown in FIGS. 30a, 30b and 30c will be apparent to the person skilled in the art. It is further noted that similar arrangements may be used for the transverse pins 98 in the embodiment of FIG. 11.

Figure 31:
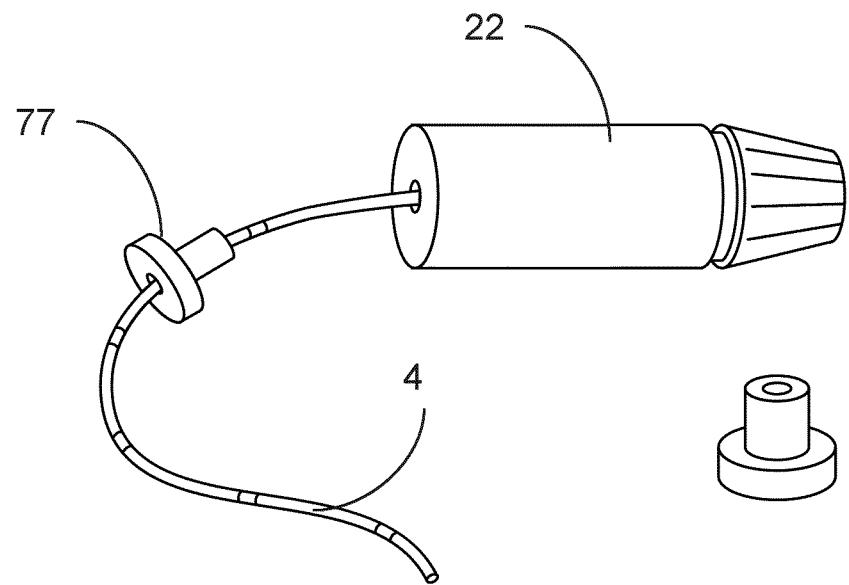
FIG. 31 shows a further example of a proximal damper for an ultrasonic activation unit.

In the embodiment of FIG. 31, a resilient plug 77 or grommet is provided that can be pushed into the proximal end of the central port 22 extending through the housing 18 and bears against the proximal part of the wire 4 extending through it. The plug 77 is designed to fit tightly into the opening of the central port 22 through which the wire 4 extends. Preferably, the plug 77 is made of rubber or a different but similarly mouldable and/or elastic material. Pushing the plug 77 into the central port 22 will cause the elastic plug 77 to be compressed and the wire 4 to be clamped, thereby further damping lateral movement of the proximal portion of the wire 4.

Figure 32:
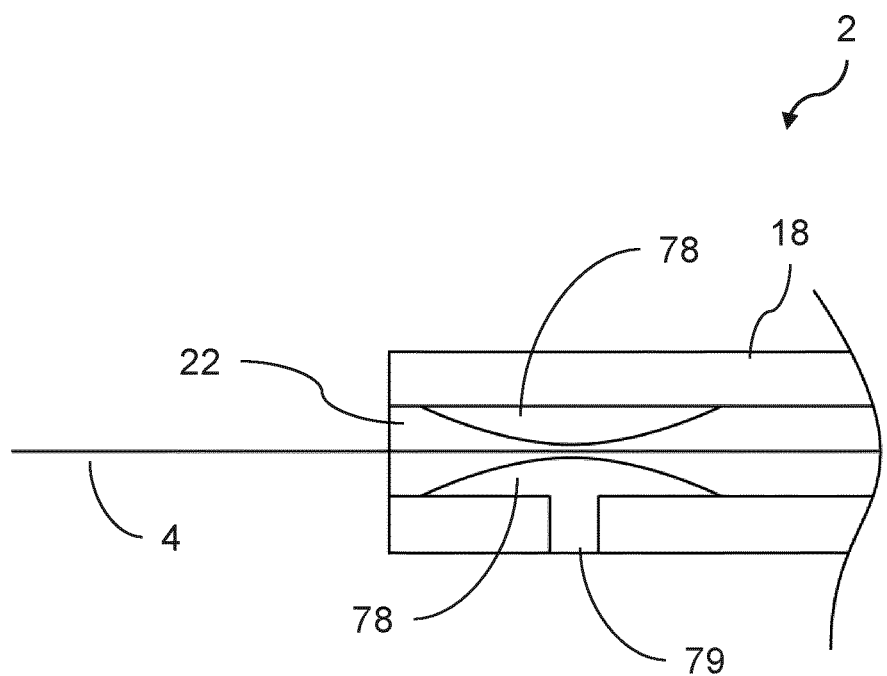
FIG. 32 shows yet another ultrasonic activation unit with proximal damping features.

In FIG. 32, a tubular flexible membrane 78 is provided within the central port 22 of the housing 18. The tubular flexible membrane 78 defines an annular chamber that can be expanded, or inflated, by the application of fluid pressure through a port 79 in the housing 18 that communicates with the chamber. The port 79 may be connected to an external fluid reservoir and a pump may pump the fluid into the tubular flexible membrane 78 to press the membrane 78 radially inwardly against the proximal part of the wire 4 to damp vibration of that part of the wire 4. When the fluid pressure is relieved, the flexible membrane 78 is deflated and the central port 22 opens up again, thereby allowing movement of the wire 4 relative to the activation unit 2 for adjustment, insertion, or removal of the wire 4. The fluid may be any type of liquid, such as water. Alternatively, the fluid may be air, in which case the membrane 78 is operated pneumatically. While the port 79 shown in FIG. 32 is arranged for connection to an external fluid reservoir, alternative embodiments may use a fluid reservoir that is integrated in the housing 18.

Most of the embodiments described above show measures for damping movement in the proximal end of the wire 4, mainly for the safety of the user and to avoid damaging expensive and sensitive equipment and indeed the wire itself. However, damping of certain wire movements may also be desirable at the distal end of the activation unit 2. Proper distal damping increases the efficiency and efficacy of the endovascular apparatus by transporting energy from the transducer to the active distal tip portion of the wire 4 predominantly by longitudinal waves without unnecessarily losing energy to lateral movements of the wire 4 along the way.

Figure 33:
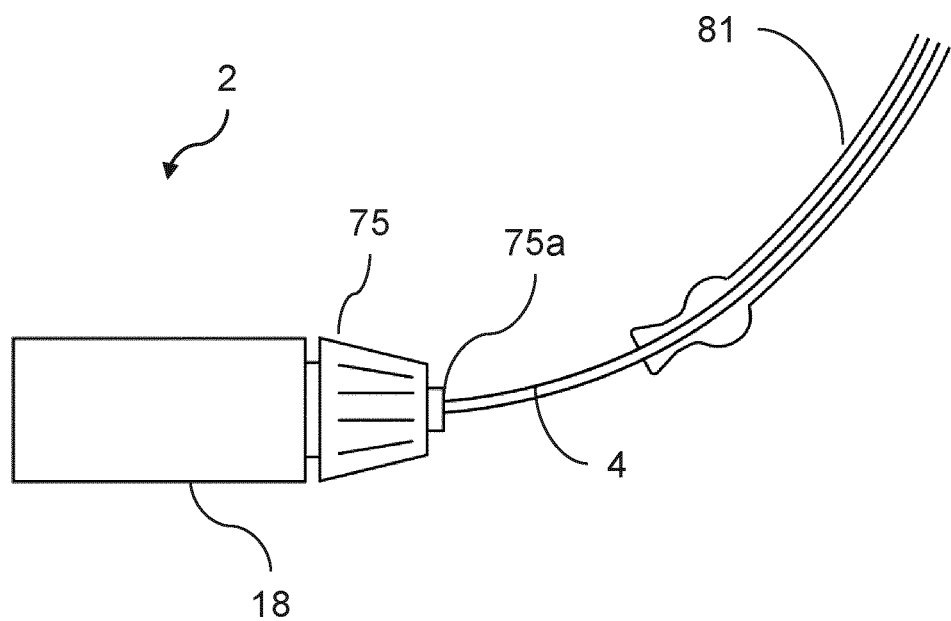
FIG. 33 shows an ultrasonic activation unit with distal damping features.

FIG. 33 shows one way in which distal damping of the wire 4 may be achieved. In this Figure, a thin sheath 81 surrounds the part of the wire 4 emerging from the distal end of the housing 18 of the activation unit 2 to damp lateral vibration of the distal part of the wire 4. The outer diameter of the sheath 81 is small enough to allow it to fit within a catheter supporting the wire 4. In an embodiment, the sheath 81 may be realised as a coating of the wire 4, such as a painted-on layer.

Figure 34A:
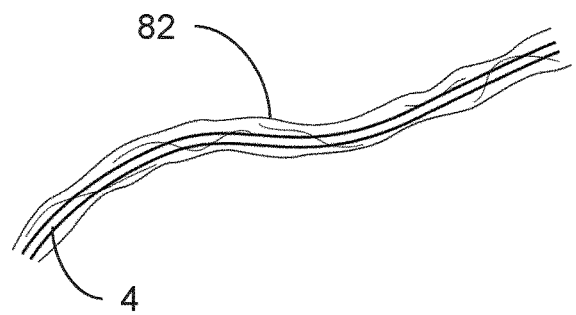
FIGS. 34a, 34b, and 34c show three examples of motion damping wire sheaths that provide for selective or intermittent damping through selective or intermittent covering or surrounding of the wire.
Figure 34B:
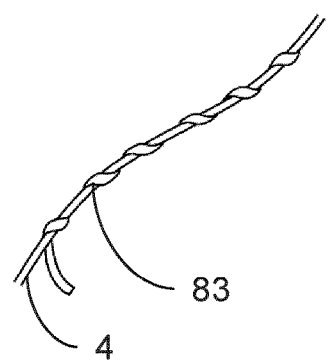
Figure 34C:
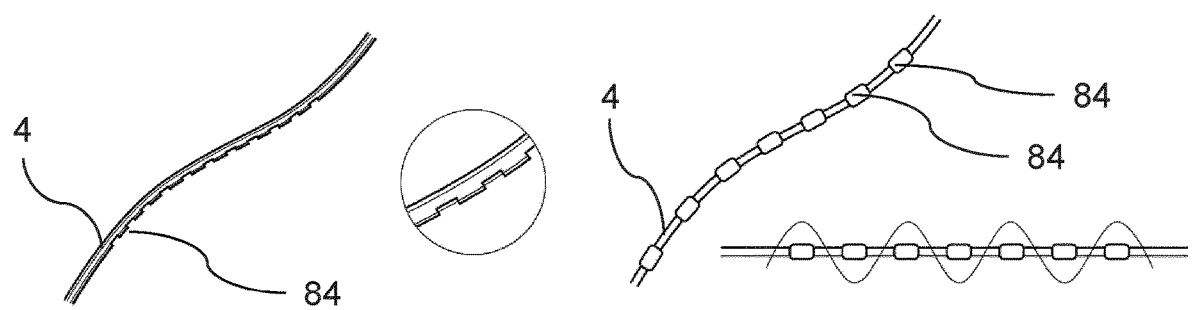

FIGS. 34a, 34b and 34c provide three variants of a catheter or sheath configured to provide proximal and/or distal damping. Each of these sheaths can be a discrete sleeve as already discussed with reference to FIG. 33. Such a discrete sleeve may either be tightly or loosely fit around the wire 4. Alternatively, the sheath may be coated or painted onto the wire 4. The sheath, sleeve, or coating can be a continuous sheath 82 as shown in FIG. 34a, a helical or spiral sheath 83 as shown in FIG. 34b, or a discontinuous or stepped sheath 84 as shown in FIG. 34c. A sheath may have cut-out windows along its length. Selective or intermittent damping may therefore be achieved through selective or intermittent covering or surrounding of the wire 4. Intermittent covering may create discrete sections of greater outer diameter than that of the wire.

All of the sheaths 82, 83, 84 have the effect of increasing the weight and inertia of the wire 4 and thereby restricting movement of the covered part of the wire 4. If displacement of the wire 4 is at its maximum at locations coincident with a damping wall section of a discontinuous or windowed sheath, this could have a positive effect on damping motion of the wire 4 as shown in FIG. 34c.

At its distal end, the sheath may be thinner than at its proximal end, such that the distal portion of the wire 4 is allowed to fit within a catheter supporting the wire 4. To maintain the possibility to translate the activation unit 2 along the wire, the sheath at the proximal end may be movable along the wire 4. Alternatively, sections of the sheathing are configured to be removable when needed. In an embodiment, the same coated or painted sheathing may be provided along the full wire 4, with a removable or movable additional sheathing at the proximal end only.

Figure 35A:
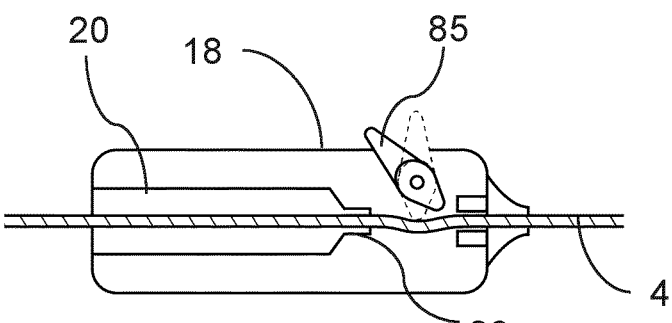
FIGS. 35a and 35b show variants of a distal damping mechanism.
Figure 35B:
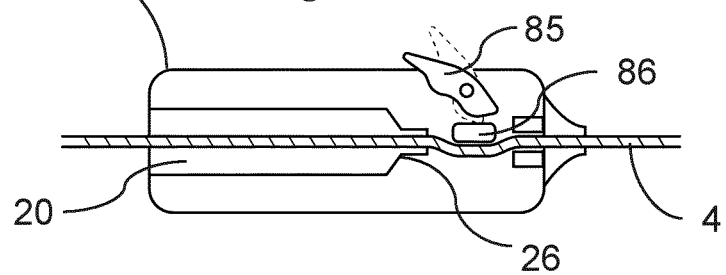

FIGS. 35a and 35b show variants of a distal damping mechanism in which a lever 85 is pivotable relative to the housing 18 to bear against a wire 4 protruding distally from the acoustic horn 26 of a transducer 20 within the housing. The lever 85 bears against a portion of the wire 4 disposed within the housing 18 between the horn 26 and the distal end of the housing 18. A strain relief feature around the wire 4 extends distally from that end of the housing 18. The lever 85 may bear against the wire 4 directly as shown in FIG. 35a or indirectly via an intermediate pad 86 interposed between the lever 85 and the wire 4 as shown in FIG. 35b.

It is noted that the many features of the various embodiments described above are not limited to those specific embodiments only. A skilled person will be able to combine features from one embodiment with features of other embodiments wherever this is technically possible and makes sense from a practical point of view.

The invention claimed is:

1. Endovascular apparatus for crossing through an obstruction in a blood vessel, the apparatus comprising:
   an elongate endovascular element,
   a source of ultrasonic energy comprising an ultrasonic transducer, and
   a coupling for, in use, transmitting the ultrasonic energy along the endovascular element from the source to an active tip portion at a distal end of the endovascular element, the coupling being arranged to couple the source to the endovascular element at any of a plurality of discrete operational positions along the length of the endovascular element for said transmission of ultrasonic energy to the active tip portion, the coupling further being arranged to clamp the endovascular element when at any of the operational positions, the endovascular element extending through the coupling and the source and having portions that extend, respectively, proximally and distally from the coupling and the source,
   wherein the endovascular apparatus further comprises damping features that are mechanically coupled to the endovascular element at positions away from the active tip portion to attenuate lateral displacement of the endovascular element proximally and distally of the transducer and to attenuate longitudinal displacement of the endovascular element proximally of the transducer.

2. An endovascular apparatus according to claim 1, wherein the ultrasonic transducer is comprised in a transducer housing.

3. An endovascular apparatus according to claim 2, wherein the transducer housing further comprises at least one of the damping features.

4. An endovascular apparatus according to claim 2, wherein at least one of the damping features is mechanically coupled to the endovascular element outside the transducer housing.

5. An endovascular apparatus according to claim 1, wherein the ultrasonic transducer comprises a lumen for holding the endovascular element, one or more of the damping features comprising at least one damper ring or damper sleeve of an elastic material, provided between the endovascular element and an inner surface of the lumen.

6. An endovascular apparatus according to claim 2, wherein the transducer housing comprises a lumen for holding the endovascular element, and wherein the damping features comprise a liquid damping medium, provided between the endovascular element and an inner surface of the lumen.

7. An endovascular apparatus according to claim 2, wherein the transducer housing comprises a distal opening, the endovascular element extending through the distal opening, and wherein the damping features comprise a damper ring or damper sleeve, provided between the endovascular element and an inner surface of the distal opening.

8. An endovascular apparatus according to claim 2, wherein the damping features comprise a plurality of guiding formations, provided in the transducer housing and arranged to be in direct contact with opposite sides of the endovascular element to prevent lateral movement of the endovascular element in a direction perpendicular to the endovascular element itself.

9. An endovascular apparatus according to claim 8, wherein the plurality of guiding formations defines a generally straight path through the transducer housing.

10. An endovascular apparatus according to claim 8, wherein the plurality of guiding formations defines a bent or undulating path through the transducer housing.

11. An endovascular apparatus according to claim 8, wherein the guiding formations are spring biased towards the endovascular element.

12. An endovascular apparatus according to claim 8, further comprising a collet, the collet surrounding the endovascular element, a proximal end of the collet being removably coupled to the ultrasonic transducer, and wherein the guiding formations are provided inside the collet.

13. An endovascular apparatus according to claim 2, further comprising a rigid tube, provided distally of the transducer housing and surrounding the endovascular element.

14. An endovascular apparatus according to claim 13, wherein the rigid tube is removably attached to the transducer housing.

15. An endovascular apparatus according to claim 13, wherein the rigid tube comprises a compressible portion.

16. An endovascular apparatus according to claim 15, wherein the compressible portion is provided at a distal tip of the rigid tube.

17. An endovascular apparatus according to claim 2, wherein the damping features comprise a flexible and elastic tubular sleeve, at least partly provided proximally of the transducer housing, the flexible and elastic tubular sleeve surrounding and holding a portion of the endovascular element.

18. An endovascular apparatus according to claim 17, wherein the damping features further comprise an adjustable clamp for selectively clamping a portion of the flexible and elastic tubular sleeve.

19. An endovascular apparatus according to claim 17, wherein the damping features further comprise an adjustable collet for selectively clamping a portion of the flexible and elastic tubular sleeve.

20. An endovascular apparatus according to claim 2, wherein the transducer housing comprises a distal opening, the endovascular element extending through the distal opening, the transducer housing further comprising a pneumatic micro-chuck for pneumatically clamping the endovascular element at the distal opening.

21. An endovascular apparatus according to claim 2, wherein the damping features comprise a set of two rotatably adjustable offset cams for clamping the endovascular element therebetween, the offset cams being provided inside the transducer housing, proximally of the transducer.

22. An endovascular apparatus according to claim 2, wherein the damping features comprise a push-button damping mechanism that can be pressed radially inwardly against the endovascular element, the push-button damping mechanism being provided inside the transducer housing, proximally of the transducer.

23. An endovascular apparatus according to claim 2, wherein the damping features comprise a rotatably adjustable proximal cap that can be turned to bring a laterally-offset spiral formation into damping contact with the endovascular element, the rotatably adjustable proximal cap being provided inside the transducer housing, proximally of the transducer.

24. An endovascular apparatus according to claim 2, wherein the damping features comprise a controllable friction collar, surrounding the endovascular element for applying an adjustable friction force thereto, the controllable friction collar being provided inside the transducer housing, proximally of the transducer.

25. An endovascular apparatus according to claim 24, wherein the transducer housing further comprises a distal toggle, operatively coupled to the controllable friction collar for adjusting the friction force.

26. An endovascular apparatus according to claim 2, wherein the damping features comprise a lever that extends longitudinally along the transducer housing, the lever being spring biased into damping contact with the endovascular element at a position proximally of the transducer.

27. An endovascular apparatus according to claim 2, wherein the transducer housing further comprises a rotatable twist-lock surrounding the endovascular element and configured to apply an adjustable clamping force thereto.

28. An endovascular apparatus according to claim 27, wherein the rotatable twist-lock is provided at a proximal end and/or at a distal end of the transducer housing.

29. An endovascular apparatus according to claim 2, wherein the damping features comprise a grommet, surrounding the endovascular element at a position proximal of the transducer housing and configured to fit into a proximal opening of the transducer housing.

30. An endovascular apparatus according to claim 1, further comprising a collet, the collet surrounding the endovascular element, a proximal end of the collet being removably coupled to the ultrasonic transducer, the damping features comprising a damper ring or damper sleeve which is provided around the endovascular element and within a distal end of the collet.

31. An endovascular apparatus according to claim 1, wherein the damping features comprise a tubular structure with a lumen for holding the endovascular element, the tubular structure comprising a fluid pocket and a flexible inner wall separating the fluid pocket from the lumen, the fluid pocket being inflatable or expandable for reducing a diameter of the lumen.

32. An endovascular apparatus according to claim 1, wherein the damping features comprise a sheath and/or a coating, surrounding at least a portion of the endovascular element distally of the transducer.

33. An endovascular apparatus according to claim 32, wherein the sheath and/or coating forms a continuous cover of the endovascular element.

34. An endovascular apparatus according to claim 32, wherein the sheath and/or coating forms a spiraling cover of the endovascular element.

35. An endovascular apparatus according to claim 32, wherein the sheath and/or coating form a discontinuous covering of the endovascular element.

36. Endovascular apparatus for crossing through an obstruction in a blood vessel, the apparatus comprising:
an elongate endovascular element,
a source of ultrasonic energy comprising an ultrasonic transducer, and
a coupling for, in use, transmitting the ultrasonic energy along the endovascular element from the source to an active tip portion at a distal end of the endovascular element, the coupling being arranged to couple the source to the endovascular element at any of a plurality of discrete operational positions along the length of the endovascular element for said transmission of ultrasonic energy to the active tip portion, the coupling further being arranged to clamp the endovascular element when at any of the operational positions, the endovascular element extending through the coupling and the source and having portions that extend, respectively, proximally and distally from the coupling and the source,
wherein the endovascular apparatus further comprises damping features that are mechanically coupled to the endovascular element to attenuate a lateral displacement of the endovascular element at positions away from the active tip portion proximally and/or distally of the transducer.

* * * * *